United States Patent [19]
Luther et al.

[11] Patent Number: 5,688,995
[45] Date of Patent: Nov. 18, 1997

[54] O-HYDROXYPHENYL-S-TRIAZINES

[75] Inventors: Helmut Luther, Grenzach-Wyhlen; Dietmar Hüglin, Freiburg; Bernd Herzog, Bad Säckingen, all of Germany

[73] Assignee: Ciba-Geigy Corporation, Tarrytown, N.Y.

[21] Appl. No.: 649,940

[22] Filed: May 15, 1996

[30] Foreign Application Priority Data

May 18, 1995 [CH] Switzerland ............... 1479/95

[51] Int. Cl.⁶ ................................. C07C 229/00
[52] U.S. Cl. ................ 562/30; 544/180; 544/216
[58] Field of Search ..................... 544/180, 216; 562/30

[56] References Cited

U.S. PATENT DOCUMENTS

| | | | |
|---|---|---|---|
| 3,118,887 | 1/1964 | Hardy et al. | 260/248 |
| 3,268,474 | 8/1966 | Hardy et al. | 260/45.8 |
| 5,476,935 | 12/1995 | Reinehr et al. | 544/180 |

FOREIGN PATENT DOCUMENTS

| | | |
|---|---|---|
| 0444323 | 9/1991 | European Pat. Off. . |
| 0648753 | 4/1995 | European Pat. Off. . |
| 0648754 | 4/1995 | European Pat. Off. . |
| 0649841 | 4/1995 | European Pat. Off. . |
| 0654469 | 5/1995 | European Pat. Off. . |
| 1469811 | 2/1969 | Germany . |
| 480090 | 12/1969 | Switzerland . |
| 2286774 | 8/1995 | United Kingdom . |

OTHER PUBLICATIONS

Derwent Abstr. 72:90534 (1970).

Primary Examiner—Terressa M. Mosley
Attorney, Agent, or Firm—Kevin T. Mansfield

[57] ABSTRACT

A description is given of o-hydroxyphenyl-s-triazines containing at least two alkoxyphenyl-substituents. They have the formula (1).

The compounds according to the invention are particularly suitable as sunscreen agents in cosmetic preparations.

8 Claims, No Drawings

O-HYDROXYPHENYL-S-TRIAZINES

The present invention relates to o-hydroxyphenyl-s-triazines containing at least two alkoxyphenyl substituents, to preparation processes for these compounds, to their use for the photochemical and thermal stabilization of dyed and undyed polyester fibre materials, to the use of these compounds as stabilizers for organic polymers, to the polymer stabilized with these compounds and to the use of these compounds as cosmetic agents.

The novel o-hydroxyphenyl-s-triazines are of the formula

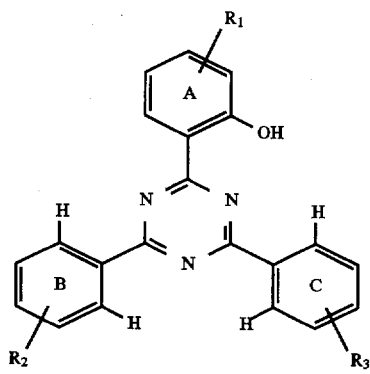

(1)

in which $R_1$ is hydrogen, hydroxyl, halogen, $C_1$–$C_{15}$alkyl, $C_1$–$C_{15}$alkoxy, a radical of the formula —O—$CH_2$—CH(—OH)—$CH_2$—O—T, in which T is $C_1$–$C_8$alkyl, or a radical of the formula

(1a)

$R_2$ and $R_3$ independently of one another are hydrogen, $C_1$–$C_{15}$alkoxy or a radical of the formula —O—$CH_2$—CH(—OH)—$CH_2$—O—T, $R_4$ is $C_1$–$C_5$alkyl or $C_1$–$C_5$alkoxy-$C_1$–$C_5$alkyl, and Q is a $C_1$–$C_4$alklene radical, the rings A, B and C can have further substituents, and the compounds must contain at least two $C_1$–$C_{15}$alkoxy radicals.

$C_1$–$C_{15}$alkyl and $C_1$–$C_{15}$alkoxy are straight-chain or branched alkyl or alkoxy radicals, respectively, such as methyl, ethyl, n-propyl, isopropyl, n-butyl, sec-butyl, tert-butyl, amyl, isoamyl or tert-amyl, heptyl, octyl, isooctyl, nonyl, decyl, undecyl, dodecyl, tetradecyl or pentadecyl, or methoxy, ethoxy, propoxy, butoxy, pentyloxy, hexyloxy, heptyloxy, octyloxy, isooctyloxy, nonyloxy, undecyloxy, dodecyloxy, tetradecyloxy or pentadecyloxy for example.

The divalent radical Q preferably contains 2 to 4 carbon atoms. Preferred divalent alkylene radicals are ethylene, ethylenepropylene or ethyleneisopropylene radicals.

Halogen is chlorine, bromine or iodine. Chlorine is preferred.

Preferred compounds of the formula (1) are those in which $R_1$ is hydrogen, hydroxyl, halogen, $C_1$–$C_{15}$alkyl or $C_1$–$C_{15}$alkoxy, or $R_2$ and $R_3$ independently of one another are hydrogen or $C_1$–$C_{15}$alkoxy, the rings A, B and C can have further substituents, and the compound must contain at least two $C_1$–$C_{15}$alkoxy radicals, and especially preferred compounds of the formula (1) are those in which the rings A and B are not substituted further or, independently of one another, are substituted by halogen, hydroxyl, $C_1$–$C_{15}$alkyl or $C_1$–$C_{15}$alkoxy.

Further preferred hydroxyphenyl-s-triazines of the formula (1) are those in which $R_1$ is hydrogen or $C_5$–$C_{15}$alkoxy; or is a radical of the formula —O—$CH_2$—CH(—OH)—$CH_2$—O—T, in which T is $C_1$–$C_8$alkyl;

$R_2$ and $R_3$ independently of one another are $C_5$–$C_{15}$alkoxy or a radical of the formula —O—$CH_2$—CH(—OH)—$CH_2$—O—T, and especially those compounds of the formula (1)

in which $R_1$ is hydrogen; and $R_2$ and $R_3$ are

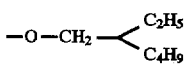

or those compounds in which $R_1$ is hydrogen or a radical of the formula (1a) and $R_2$ and $R_3$ are $C_5$–$C_{15}$alkoxy, especially $C_5$–$C_8$alkoxy, or a radical of the formula —O—$CH_2$—CH(—OH)—$CH_2$—O—T.

Examples of compounds of the formula (1) which may be mentioned are:

2-(2'-hydroxyphenyl)-4,6-bis(4-methoxyphenyl)-1,3,5-triazine;

2-(2',4'-dihydroxyphenyl)-4,6-bis(4-methoxyphenyl)-1,3,5-triazine;

2-(2'-hydroxy-3'-methylphenyl)-4,6-bis(4-methoxyphenyl)-1,3,5-triazine;

2-(2',3'-dihydroxyphenyl)-4,6-bis(4-methoxyphenyl)-1,3,5-triazine;

2-(2'-hydroxy-5'-chlorophenyl)-4,6-bis(4-methoxyphenyl)-1,3,5-triazine;

2-(2'-hydroxy-4-methoxyphenyl)-4,6-bis(4-methoxyphenyl)-1,3,5-triazine;

2-(2',4'-dihydroxyphenyl)-4,6-bis(4-methoxyphenyl)-1,3,5-triazine;

2-(2'-hydroxy-4-hexyloxyphenyl)-4,6-bis(4-methoxyphenyl)-1,3,5-triazine;

2-(2'-hydroxy-4-hexyloxyphenyl)-4,6-bis(3-methoxyphenyl)-1,3,5-triazine;

2-(2-hydroxy-4-methoxyphenyl)-4-(4-methoxyphenyl)-6-phenyl-1,3,5-triazine;

2-(2'-hydroxy-4'-[2-ethylhexyloxy])-4,6-bis-(2-ethylhexyloxy)phenyl-1,3,5-triazine;

2-(2'-hydroxy)-4,6-bis-4'-[2-ethylhexyloxy]phenyl-1,3,5-triazine.

The compounds of the formula (1) can be prepared by various methods.

For example, the compounds of the formula (1) can be prepared in a one-step process by reacting a salicylic compound with a benzamidine compound. The preparation process comprises reacting a salicylic compound of the formula

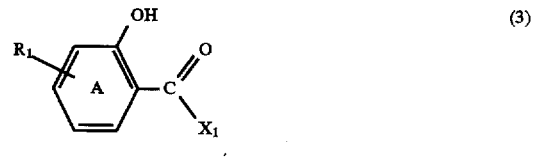

(3)

with a benzamidine compound of the formula

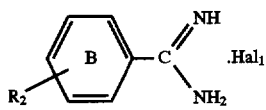

to give the triazine compound of the formula (1), where $R_1$, $R_2$, A and B are as defined for formula (1), $X_1$ is halogen or —$OR_4$, $R_4$ is $C_1$–$C_3$alkyl, and $Hal_1$ is halogen.

The starting compounds of the formula (3) are substituted or unsubstituted salicylic esters or salicyloyl halides, for example methyl, ethyl or propyl salicylate, or salicyloyl chloride or bromide, which may be substituted in the phenyl radical by further radicals in accordance with the definition of A.

In the process according to the invention, the starting compounds of the formulae (3) and (4) can be used in different molar ratios.

The molar ratios of the compound of the formula (3) to the compound of the formula (4) are preferably from 1:10 to 10:1.

Where the starting compound of the formula (3) is a salicyloyl halide ($X_1$=halogen) the molar ratio of the compound of the formula (3) to the compound of the formula (4) is preferably from 1:3 to 1:2.

If the starting compound of the formula (3) employed is a salicylic ester ($X_1$=—$OR_4$) the molar ratio of the compound of the formula (3) to the compound of the formula (4) is preferably from 2:1 to 1:2.

Suitable benzamidine compounds of the formula (4) are benzamidine hydrobromide and, preferably, benzamidine hydrochloride, which may be further substituted in the phenyl radical in accordance with the definition of B. These compounds are usually used as the solid products having an active substance content of about 90–95%.

When the starting compound of the formula (3) used is a salicyloyl halide ($X_1$=halogen), at least the calculated quantity of a base is usually added in order to neutralize the acid formed during the reaction. The bases used can be either organic or inorganic compounds, for example alkali metal hydroxide, in particular sodium hydroxide, potassium hydroxide solution; aqueous ammonia solution; ammonia gas; alkali metal carbonate, especially sodium carbonate or potassium carbonate; sodium acetate; tertiary amines, such as pyridine or trialkylamines, in particular triethylamine, N,N-dimethylcyclohexylamine, N,N-dimethylaniline; alkali metal alkylates, especially sodium methylate, potassium methylate or potassium tert-butylate.

The process according to the invention is generally carried out in such a manner that the salicylic compound and the benzamidine compound are first introduced in an inert solvent.

Suitable inert solvents in this context are aliphatic hydrocarbons and mixtures thereof, for example cyclohexane or aromatic hydrocarbons such as toluene, or dimethylacetamide, or mixtures of these solvents.

Where the starting compound of the formula (3) used is a salicyloyl halide ($X_1$=Hal), it is also possible to add a further solvent, generally a polar solvent, for example acetonitrile or dioxane.

The reaction time for the process according to the invention is in general 2 to 30 hours. Depending on whether the starting compound of the formula (3) used is a salicyloyl halide ($X_1$=Hal) or a salicylic ester ($X_1$=—$OR_4$), the reaction times may vary. When using a salicylic ester, the reaction time is preferably from 4 to 30 hours, in particular from 18 to 22 hours. If a salicyloyl halide is used, the reaction times are somewhat shorter. They are preferably from 2 to 20 hours, in particular from 4 to 8 hours.

The reactions are generally slightly exothermic. However, a reaction temperature of 95 C. should not be exceeded, since higher temperatures may lead to the formation of by-products, for example nitrile compounds from the benzamidines. In practice, the reaction is carried out in a temperature range from 60 to 95 C., preferably from 80 to 95 C.

The compounds of the formula (1) according to the invention can also be prepared by dehydrogenating a dihydrotriazine compound of the formula

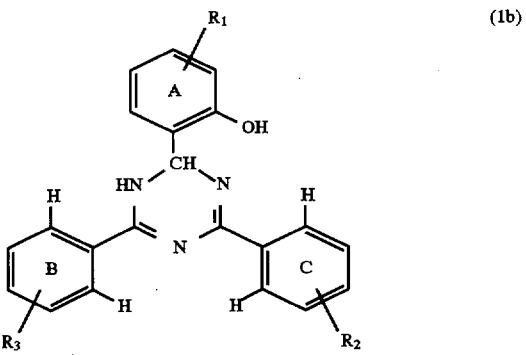

in which $R_1$, $R_2$, $R_3$, A, B and C are as defined for formula (1).

The dehydrogenating agent employed is generally chloranil. The dehydrogenation of dihydrotriazine compounds with chloranil to give 1,3,5-triazines is known, for example, from Khim. Geteritsikl. Soedin. (2), p. 350–353 (1969).

The starting compounds of the formula (1b) are prepared in a manner known per se by reacting 2 mol of a suitable benzamidine hydrohalide compound with one mole of a suitable α-hydroxybenzaldehyde compound.

Another way of preparing triazine compounds of the formula (1) is to react a monochlorotriazine compound of the formula

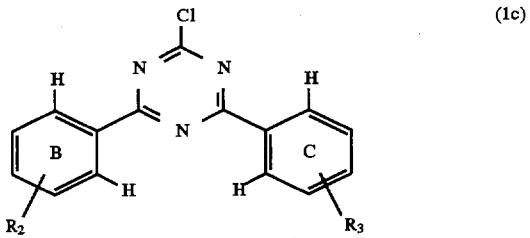

with an α-hydroxyphenyl compound of the formula

in the presence of a Lewis acid, especially aluminium chloride.

In these formulae, $R_1$, $R_2$, $R_3$, A, B and C are as defined for formula (1). This reaction is known, for example, from J. Am. Chem. Soc. 73(7) (1951 ).

The starting compounds of the formula (1c) can be prepared in a manner known per se, for example by reacting cyanuric chloride and the corresponding phenylmagnesium bromide compounds in a Grignard reaction. This reaction has been disclosed, for example, by Hirt et al., Helv. Chim. Acta, 33, 1368 (1950).

The triazine compounds according to the invention can also be prepared by reacting an areno-oxazinone compound of the formula

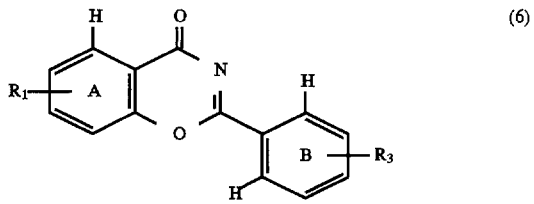

with a benzamidine compound of the formula (4). In this formula $R_1$, $R_2$, $R_3$, $Hal_1$, A, B and C are as defined.

The areno-oxazinone compounds of the formula (6) and the preparation of these compounds are known, for example, from GB-B-1,155,506.

The compounds of the formula (1) are suitable as UV stabilizers, i.e. for protecting organic materials which are sensitive to ultraviolet light, and especially for protecting textile fibre materials against the damaging effect of ultraviolet radiation.

Accordingly, the invention also provides a process for the dyeing or printing and photochemical and thermal stabilization of polyester fibre materials. The process comprises treating the fibre material by adding a compound of the formula (1) to the aqueous dyeing liquor or printing paste.

The triazine compounds of the formula (1) according to the invention are used in this process in a quantity of from 0.01 to 10% by weight, preferably from 0.1 to 5% by weight, based on the weight of the fibre material.

The triazine compounds of the formula (1) are of low solubility in water and are therefore applied in dispersed form. For this purpose they are milled with an appropriate dispersant to a fineness of about 1–2 μm using, for example, a quartz ball mill or a high-speed stirrer.

Examples of suitable dispersants for the compounds of the formula (1) are:

acidic esters or salts thereof of alkylene oxide adducts, for example acidic esters or salts thereof of a polyadduct of from 4 to 40 mol of ethylene oxide with 1 mol of a phenol; or phosphoric esters of the adducts of from 6 to 30 mol of ethylene oxide with 1 mol of 4-nonylphenol, 1 mol of dinonylphenol or, in particular, with 1 mol of compounds which are prepared by the addition reaction of from 1 to 3 mol of substituted or unsubstituted styrenes with 1 mol of phenol, polystyrene sulfonates, fatty acid taurides, alkylated diphenyl oxide mono- or disulfonates, sulfonates of polycarboxylic acid esters, adducts of 1 to 60 mol, preferably 2 to 30 mol, of ethylene oxide and/or propylene oxide with fatty amines, fatty amides, fatty acids or fatty alcohols each having 8 to 22 carbon atoms, or with trihydric to hexahydric alkanols having 3 to 6 carbon atoms, said adducts being converted into an acidic ester with an organic dicarboxylic acid or with an inorganic polybasic acid, ligninsulfonates, and, very particularly, formaldehyde condensation products, for example condensation products of ligninsulfonates and/or phenol and formaldehyde, condensation products of formaldehyde with aromatic sulfonic acids, such as condensation products of ditolyl ether sulfonates and formaldehyde, condensation products of naphthalenesulfonic acid and/or naphthol- or naphthylaminesulfonic acids with formaldehyde, condensation products of phenolsulfonic acids and/or sulfonated dihydroxydiphenyl sulfone and phenols and/or cresols with formaldehyde and/or urea, and condensation products of diphenyl oxide disulfonic acid derivatives with formaldehyde.

Suitable dyes are disperse dyes which are of only low solubility in water. In the dyeing liquor they are therefore present predominantly in the form of a fine dispersion. They may belong to various classes of dyes, for example the acridone, azo, anthraquinone, coumarin, methine, perinone, naphthoquinonimine, quinophthalone, styryl or nitro dyes. It is also possible in accordance with the invention to employ mixtures of disperse dyes.

Examples of the polyester fibre material which can be dyed or printed and treated using the abovementioned triazine compounds are cellulose ester fibres, for example cellulose acetate and cellulose triacetate fibres, and especially linear polyester fibres which may also have undergone acid modification, which fibres are obtained, for example, by condensation of terephthalic acid with ethylene glycol or of isophthalic acid or terephthalic acid with 1,4-bis (hydroxymethyl)cyclohexane, and also fibres made from copolymers of terephthalic and isophthalic acid and ethylene glycol. The linear polyester fibre material which has so far been employed almost exclusively in the textile industry consists of terephthalic acid and ethylene glycol.

The fibre materials can also be used as blend fabrics with themselves or with other fibres, for example blends of polyacrylonitrile/polyester, polyamide/polyester, polyester/cotton, polyester/viscose and polyester/wool, and can be discontinuously or continuously dyed or else printed by known methods.

The textile material can be present in various make-up forms. Preferred forms are piece goods, such as knitted or woven pieces, or else yarn on cheeses, warp beams and the like.

Also highly suitable for the process according to the invention are light-pervious textile fabrics in the outerwear garment sector. When treated by the process according to the invention, such textiles are capable of protecting the skin tissue underneath the transparent outerwear fabric against the damaging effect of UV radiation.

Dyeing is carried out from an aqueous liquor by a continuous or batchwise method. In the batchwise method, the liquor ratio can be selected within a wide range, for example from 4:1 to 100:1, preferably from 6:1 to 50:1. The temperature at which the dyeing is carried out is at least 50 C. and is usually not higher than 140 C. The preferred temperature range is from 80 to 135 C.

In the case of continuous dyeing methods, the dyeing liquors, which, if desired, may apart from the dyes contain further auxiliaries, are applied to the piece material by, for example, padding or face padding, and the dyes are fixed by thermofixing or HT steaming processes, for example at from 190 to 230 C. for from 30 seconds to 3 minutes.

Linear polyester fibres and polyester blend fibres are preferably dyed by the so-called high-temperature method in closed and pressure-resistant apparatus at temperatures >100 C., preferably between 110 and 135 C., and, if desired, under pressure. Examples of suitable closed vessels are circulation apparatus, such as package-dyeing or beam-dyeing machines, winch becks, jet- or drum-dyeing machines, muff-dyeing machines, paddles or jiggers.

Secondary cellulose acetate fibres are preferably dyed at temperatures of 80–85 C.

The UV stabilizers according to the invention can be used in the dyeing application before or after dyeing or else, preferably, by treating the fibre material simultaneously with the UV stabilizer and the dye in the dyebath.

The dyeing liquors can also contain further additives, for example dyeing assistants, dispersants, carriers, wool-protecting agents, wetting agents and antifoams.

Furthermore, the dyebaths can contain mineral acids, for example sulfuric acid or phosphoric acid, or, advantageously, organic acids, for example aliphatic carboxylic acids such as formic acid, acetic acid, oxalic acid or citric acid, and/or salts such as ammonium acetate, ammonium sulfate or sodium acetate. The purpose of the acids is in particular to adjust the pH of the liquors used in accordance with the invention, which is preferably between 4 and 5.

Preferably, the fibre material is first pretreated in the bath which contains the dye, the UV stabilizer and any other additives and is adjusted to a pH of from 4.5 to 5.5, at from 40 to 80 C. for 5 minutes, then the temperature is increased to 125 to 130 C. over the course of 10 to 20 minutes, and treatment continues at this temperature for 15 to 90 minutes, preferably 30 minutes.

The dyeings are finished by cooling the dyeing liquor to 50 to 80 C., rinsing the dyeings with water and, if desired, by reduction-cleaning them in a customary manner in an alkaline medium. The dyeings are then again rinsed and dried. When vat dyes are used for the cellulose portion, the material is first treated in a customary manner with hydrosulfite at a pH of from 6 to 12.5 and then with an oxidizing agent, and finally is rinsed with water.

To produce prints, the triazine compounds according to the invention are admixed to the printing pastes in the form of their aqueous dispersions.

The printing paste contains the corresponding triazine compound in quantities of from 0.1 to 10%, preferably from 0.1 to 5%, based on the weight of the printing paste.

The amount of dyes added to the printing pastes depends on the desired shade. In general, amounts of from 0.01 to 15 percent, preferably from 0.02 to 10 percent, by weight based on the textile material employed, have proved to be advantageous.

In addition to the dyes and the aqueous UV stabilizer dispersion, the printing pastes advantageously comprise acid-stable thickeners, preferably of natural origin, such as kernel flour derivatives, in particular sodium alginate by itself or in a mixture with modified cellulose, especially with, preferably, from 20 to 25 percent by weight of carboxymethylcellulose. In addition, the printing pastes can also comprise acid donors, such as butyrolactone or sodium hydrogen phosphate, preservatives, sequestering agents, emulsifiers, water-insoluble solvents, oxidizing agents or deaerating agents.

Suitable preservatives are, in particular, formaldehyde-releasing agents, for example paraformaldehyde or trioxane, especially aqueous solutions of formaldehyde with a concentration of about 30 to 40 percent by weight; examples of suitable sequestering agents are sodium nitrilotriacetate, sodium ethylenediaminetetraacetate, especially sodium polymetaphosphate, and in particular sodium hexametaphosphate; suitable emulsifiers are, in particular, adducts of an alkylene oxide and a fatty alcohol, especially an adduct of oleyl alcohol and ethylene oxide; suitable water-insoluble solvents are high-boiling, saturated hydrocarbons, especially paraffins with a boiling range of about 160 to 210 C. (white spirit); examples of suitable oxidizing agents are an aromatic nitro compound, especially an aromatic mono- or dinitro-carboxylic acid or -sulfonic acid which, if desired, may be present as an alkylene oxide adduct, in particular a nitrobenzene sulfonic acid; and examples of suitable deaerating agents are high-boiling solvents, especially turpentine oils, higher alcohols, preferably $C_8$ to $C_{10}$ alcohols, terpene alcohols or deaerating agents based on mineral oils and/or silicone oils, especially commercial formulations comprising from about 15 to 25 percent by weight of a mineral oil/silicone oil mixture and from about 75 to 85 percent by weight of a $C_8$ alcohol, for example 2-ethyl-n-hexanol.

When printing the fibre materials, the printing paste is directly applied to all or part of the surface of the fibre material, advantageously using printing machines of customary design, for example intaglio printing, rotary screen printing and flat screen printing machines.

After printing, the fibre material is dried at temperatures of up to 150 C., preferably from 80 to 120 C.

Fixing is then carried out by subjecting the material to a heat treatment at temperatures of preferably from 100 to 220 C. The heat treatment is generally carried out with superheated steam under pressure.

Depending on the temperature, fixing may be carried out for 20 seconds to 10 minutes, preferably 4 to 8 minutes.

The prints are finished likewise in a customary manner by rinsing them with water, followed, if desired, by additional reduction-cleaning in an alkaline medium by means, for example, of sodium dithionite. In the latter case the prints are again rinsed, hydroextracted and dried.

With the process according to the invention it is possible to obtain polyester dyeings and prints of high lightfastness and sublimation fastness. Selected pretreatment or aftertreatment of the fibre material is not necessary in the process according to the invention.

The compounds of the formula (1) can be used advantageously as stabilizers for organic polymers to counter their damage by light, oxygen and heat. Accordingly, the invention also provides a process for stabilizing organic polymers against damage by light, oxygen and heat, which comprises admixing at least one compound of the formula (1) to these materials. Examples of such polymers to be stabilized are:

1. Polymers of monoolefins and diolefins, for example polypropylene, polyisobutylene, polybut-1-ene, poly-4-methylpent-1-ene, polyisoprene or polybutadiene, as well as polymers of cycloolefins, for example of cyclopentene or norbornene; furthermore polyethylene (which optionally can be crosslinked), for example high density polyethylene (HDPE), low density polyethylene (LDPE), linear low density polyethylene (LLDPE), branched low density polyethylene (BLDPE).

Polyolefins, i.e. polymers of monoolefins exemplified in the preceding paragraph, in particular polyethylene and polypropylene, can be prepared by different, and especially by the following, methods:

a) radical polymerization (normally under high pressure and at elevated temperature)

b) catalytic polymerization using a catalyst that normally contains one or more metals of group IVb, Vb, VIb or VIII of the Periodic Table. These metals usually have one or more ligands, such as oxides, halides, alcoholates, esters, ethers, amines, alkyls, alkenyls and/or aryls that may be either π- or σ-coordinated. These metal complexes may be in the free form or fixed on substrates, for example on activated magnesium chloride, titanium(III) chloride, alumina or silicon oxide. These catalysts may be soluble or insoluble in the polymerization medium. The catalysts can be active as such in the polymerization or further activators may be used, for example metal alkyls, metal hydrides, metal alkyl halides, metal alkyl oxides or metal alkyloxanes, the metals being elements of groups Ia, IIa and/or IIIa of the Periodic Table. The activators may be modified, for example, with further ester, ether, amine or silyl ether groups. These catalyst systems are usually termed Phillips, Standard Oil Indiana, Ziegler (-Natta), TNZ (DuPont), metallocene or single site catalysts (SSC).

2. Mixtures of the polymers mentioned under 1 ), for example mixtures of polypropylene with polyisobutylene, polypropylene with polyethylene (for example PP/HDPE, PP/LDPE) and mixtures of different types of polyethylene (for example LDPE/HDPE). 3. Copolymers of monoolefins and diolefins with each other or with other vinyl monomers, for example ethylene-propylene copolymers, linear low density polyethylene (LLDPE) and mixtures thereof with low density polyethylene (LDPE), propylene-but-1-ene copolymers, propylene-isobutylene copolymers, ethylene-but-1-ene copolymers, ethylene-hexene copolymers, ethylene-methylpentene copolymers, ethylene-heptene copolymers, ethylene-octene copolymers, propylene-butadiene copolymers, isobutylene-isoprene copolymers, ethylene-alkyl acrylate copolymers, ethylene-alkyl methacrylate copolymers, ethylene-vinyl acetate copolymers and their copolymers with carbon monoxide or ethylene-acrylic acid copolymers and their salts (ionomers) as well as terpolymers of ethylene with propylene and a diene such as hexadiene, dicyclopentadiene or ethylidene-norbornene; and mixtures of such copolymers with one another and with polymers mentioned under 1 ), for example polypropylene-ethylene-propylene copolymers, LDPE-ethylene-vinyl acetate copolymers, LDPE-ethylene-acrylic acid copolymers, LLDPE-ethylene-vinyl acetate copolymers, LLDPE-ethylene-acrylic acid copolymers and alternating or random polyalkylene-carbon monoxide copolymers and mixtures thereof with other polymers, for example polyamides.

4. Hydrocarbon resins (for example $C_5$–$C_9$) including hydrogenated modifications thereof (e.g. tackifier resins) and mixtures of polyalkylenes and starch.

5. Polystyrene poly(p-methylstyrene), poly($\alpha$-methylstyrene).

6. Copolymers of styrene or $\alpha$-methylstyrene with dienes or acrylic derivatives, for example styrene-butadiene, styrene-acrylonitrile, styrene-alkyl methacrylate, styrene-butadiene-alkyl acrylate, styrene-butadiene-alkyl methacrylate, styrene-maleic anhydride, styrene-acrylonitrile-methyl acrylate; mixtures of high impact strength of styrene copolymers and another polymer, for example a polyacrylate, a diene polymer or an ethylene-propylene-diene terpolymer, and block copolymers of styrene such as styrene-butadiene-styrene, styrene-isoprene-styrene, styrene-ethylene-butylene-styrene or styrene-ethylene-propylene-styrene.

7. Graft copolymers of styrene or $\alpha$-methylstyrene, for example styrene on polybutadiene, styrene on polybutadiene-styrene or polybutadiene-acrylonitrile copolymers, styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene, styrene and alkyl acrylates or alkyl methacrylates on polybutadiene, styrene and acrylonitrile on ethylene-propylene-diene terpolymers, styrene and acrylonitrile on polyalkyl acrylates or polyalkyl methacrylates, styrene and acrylonitrile on acrylate-butadiene copolymers, as well as mixtures thereof with the copolymers mentioned under 6), for example the copolymer mixtures known as ABS, MBS, ASA or AES polymers.

8. Halogen-containing polymers such as polychloroprene, chlorinated rubber, chlorinated or sulfochlorinated polyethylene, copolymers of ethylene and chlorinated ethylene, epichlorohydrin homo- and copolymers, especially polymers of halogen-containing vinyl compounds, for example polyvinyl chloride, polyvinylidene chloride, polyvinyl fluoride, polyvinylidene fluoride; as well as copolymers thereof such as vinyl chloride-vinylidene chloride, vinyl chloride-vinyl acetate or vinylidene chloride-vinyl acetate.

9. Polymers derived from $\alpha,\beta$-unsaturated acids and derivatives thereof such as polyacrylates and polymethacrylates, polymethyl methacrylates, polyacrylamides and polyacrylonitriles, impact-modified with butyl acrylate.

10. Copolymers of the monomers mentioned under 9) with each other or with other unsaturated monomers, for example acrylonitrile-butadiene copolymers, acrylonitrile-alkyl acrylate copolymers, acrylonitrile-alkoxyalkyl acrylate copolymers, acrylonitrile-vinyl halide copolymers or acrylonitrile-alkyl methacrylate-butadiene terpolymers.

11. Polymers derived from unsaturated alcohols and amines or the acyl derivatives or acetals thereof, such as polyvinyl alcohol, polyvinyl acetate, polyvinyl stearate, polyvinyl benzoate, polyvinyl maleate, polyvinyl butyral, polyallyl phthalate or polyallyl melamine; as well as their copolymers with olefins mentioned in point 1.

12. Homopolymers and copolymers of cyclic ethers such as polyalkylene glycols, polyethylene oxide, polypropylene oxide or copolymers thereof with bisglycidyl ethers.

13. Polyacetals such as polyoxymethylene and those polyoxymethylenes which contain comonomers, for example ethylene oxide; polyacetals modified with thermoplastic polyurethanes, acrylates or MBS.

14. Polyphenylene oxides and sulfides, and mixtures thereof with styrene polymers or polyamides.

15. Polyurethanes derived from hydroxyl-terminated polyethers, polyesters and polybutadienes on the one hand and aliphatic or aromatic polyisocyanates on the other, as well as precursors thereof.

16. Polyamides and copolyamides derived from diamines and dicarboxylic acids and/or from aminocarboxylic acids or the corresponding lactams, such as polyamide 4, 6, 6/6, 6/10, 6/9, 6/12, 4/6, 12/12,11 and 12, aromatic polyamides starting from m-xylene, diamine and adipic acid; polyamides prepared from hexamethylenediamine and isophthalic and/or terephthalic acid and with or without an elastomer as modifier, for example poly-2,4,4-trimethylhexamethylene terephthalamide or poly-m-phenylene isophthalamide. Block copolymers of the aforementioned polyamides with polyolefins, olefin copolymers, ionomers or chemically bonded or grafted elastomers; or with polyethers, e.g. with polyethylene glycol, polypropylene glycol or polytetramethylene glycol. As well as polyamides or copolyamides modified with EPDM or ABS; and polyamides condensed during processing (RIM polyamide systems).

17. Polyureas, polyimides, polyamide-imides and polybenzimidazoles.

18. Polyesters derived from dicarboxylic acids and dialcohols and/or from hydroxycarboxylic acids or the corresponding lactones, such as polyethylene terephthalate, polybutylene terephthalate, poly-1,4-dimethylolcyclohexane terephthalate, polyhydroxybenzoates, as well as block polyether esters derived from hydroxyl-terminated polyethers; and also polyesters modified with polycarbonates or MBS.
19. Polycarbonates and polyester carbonates.
20. Polysulfones, polyether sulfones and polyether ketones.
21. Crosslinked polymers derived from aldehydes on the one hand and phenols, urea or melamine on the other hand, such as phenol/formaldehyde resins, urea/formaldehyde resins and melamine/formaldehyde resins.
22. Drying and non-drying alkyd resins.
23. Unsaturated polyester resins derived from copolyesters of saturated and unsaturated dicarboxylic acids with polyhydric alcohols and vinyl compounds as crosslinking agents, and also halogen-containing modifications thereof of low flammability.
24. Crosslinkable acrylic resins derived from substituted acrylates, for example from epoxy acrylates, urethane acrylates or polyester acrylates.
25. Alkyd resins, polyester resins and acrylate resins crosslinked with melamine resins, urea resins, polyisocyanates or epoxy resins.
26. Crosslinked epoxy resins derived from polyepoxides, for example from bisglycidyl ethers, or cycloaliphatic diepoxides.
27. Natural polymers such as cellulose, natural rubber, gelatin and derivatives thereof which have been chemically modified in a polymer-homologous manner, for example cellulose acetates, cellulose propionates and cellulose butyrates, or the cellulose ethers such as methyl cellulose; as well as rosins and derivatives.
28. Blends (polyblends) of the aforementioned polymers, for example PP/EPDM, polyamide/EPDM or ABS, PVC/EVA, PVC/ABS, PVC/MBS, PC/ABS PBTP/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA 6.6 and copolymers, PA/HDPE, PA/PP or PA/PPO.

Particular preference is given to the use of compounds according to the invention as stabilizers in coating materials of any type. This also means a process in accordance with the above description, in which the organic polymer is a binder for a coating material. The coating materials may be pigmented or unpigmented coatings or metallic effect paints. They may contain an organic solvent or may be solvent-free, or may be aqueous coating materials.

The coatings can contain as binder at least one of the polymers listed above. Examples of coatings containing specific binders are as follows:
1. coatings based on cold- or hot-crosslinkable alkyd, acrylate, polyester, epoxy or melamine resins or mixtures of such resins, where appropriate with the addition of an acidic curing catalyst;
2. two-component polyurethane coatings based on hydroxyl-containing acrylate, polyester or polyether resins and aliphatic or aromatic polyisocyanates;
3. one-component polyurethane coatings based on blocked polyisocyanates which are unblocked during stoving;
4. two-component coatings based on (poly)ketimines and aliphatic or aromatic polyisocyanates;
5. two-component coatings based on (poly)ketimines and an unsaturated acrylate resin or a polyacetoacetate resin or a methyl methacrylamidoglycolate;
6. two-component coatings based on carboxyl- or amino-containing polyacrylates and polyepoxides;
7. two-component coatings based on acrylate resins containing anhydride groups and on a polyhydroxyl or polyamino component;
8. two-component coatings based on (poly)oxazolidines and on acrylate resins containing anhydride groups, or on unsaturated acrylate resins or aliphatic or aromatic polyisocyanates;
9. two-component coatings based on unsaturated polyacrylates and polymalonates;
10. thermoplastic polyacrylate coatings based on thermoplastic acrylate resins or externally crosslinking acrylate resins in combination with etherified melamine resins; and
11. coating systems based on siloxane-modified or fluorine-modified acrylate resins.

The coatings can also be radiation-curable materials. In this case, the binder comprises monomeric or oligomeric compounds which contain ethylenic double bonds and are converted into a crosslinked, high molecular weight form by irradiation with actinic light or with electron beams. In such cases the binder is usually a mixture of such compounds.

The coatings can be applied in a single coat or in two coats, the stabilizers according to the invention preferably being added to the unpigmented uppermost coat.

The coatings can be applied to the substrates (metal, plastic, wood, etc.) by the customary method, for example by brushing, spraying, flowcoating, dipping or electrophoresis.

The quantity of the stabilizer of the formula (1) added depends on the respective substrate and on its intended use. In general, quantities of from 0.01 to 5% by weight are sufficient, with preference being given to the use of from 0.05 to 3% by weight based on the polymer to be stabilized. According to the invention, polymers containing from 0.01 to 5% by weight, especially from 0.05 to 3% by weight, of at least one compound of the formula (1) are therefore particularly suitable.

In certain cases it may be advantageous to use two or more compounds of the formula (1). In addition, one or more other stabilizers and/or other additives may be included, for example the following types of compounds:
1. Antioxidants
  1.1. Alkylated monophenols, for example 2,6-di-tert-butyl-4-methylphenol, 2-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(α-methylcyclohexyl)-4,6-dimethylphenol, 2,6-dioctadecyl-4-methylphenol, 2,4,6-tricyclohexylphenol, 2,6-di-tert-butyl-4-methoxymethylphenol, 2,6-di-nonyl-4-methylphenol, 2,4-dimethyl-6-(1-methylundec-1'-yl)-phenol, 2,4-dimethyl-6-(1'-methylheptadec-1'-yl)-phenol, 2,4-dimethyl-6-(1'-methyl tridec-1'-yl)phenol and mixtures thereof.
  1.2. Alkylthiomethylphenols, for example 2,4-dioctylthiomethyl-6-tert-butylphenol, 2,4-dioctylthiomethyl-6-methylphenol, 2,4-dioctylthiomethyl-6-ethylphenol, 2,6-didodecylthiomethyl-4-nonylphenol.
  1.3. Hydroquinones and alkylated hydroquinones, for example 2,6-di-tert-butyl-4-methoxyphenol, 2,5-di-tert-butylhydroquinone, 2,5-di-tert-amylhydroquinone, 2,6-diphenyl-4-octadecyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenyl stearate, bis(3,5-di-tert-butyl-4-hydroxyphenyl)adipate.
  1.4. Hydroxylated thiodiphenyl ethers, for example 2,2'-thiobis(6-tert-butyl-4-methylphenol), 2,2'-thiobis(4- octylphenol), 4,4'-thiobis(6-tert-butyl-3-methylphenol), 4,4'-thiobis(6-tert-butyl-2-methylphenol), 4,4'-thiobis(3,6-di-sec-amylphenol), 4,4'-bis(2,6-dimethyl-4-hydroxyphenyl)disulfide.

1.5. Alkylidenebisphenols, for example 2,2'-methylenebis(6-tert-butyl-4-methylphenol), 2,2'-methylenebis(6-tert-butyl-4-ethylphenol), 2,2'-methylenebis[4-methyl-6-(α-methylcyclohexyl)-phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-(α-methylbenzyl)-4-nonylphenol], 2,2'-methylenebis[6-(α,α-dimethylbenzyl)-4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methylphenyl)-3-n-dodecylmercaptobutane, ethylene glycol bis[3,3-bis(3'-tert-butyl-4'-hydroxyphenyl)butyrate], bis(3-tert-butyl-4-hydroxy-5-methylphenyl)dicyclopentadiene, bis[2-(3'-tert-butyl-2'-hydroxy-5'-methylbenzyl)-6-tert-butyl-4-methylphenyl]terephthalate, 1,1-bis(3,5-dimethyl-2-hydroxyphenyl)butane, 2,2-bis(3,5-di-tert-butyl-4-hydroxyphenyl)propane, 2,2-bis(5-tert-butyl-4-hydroxy-2-methylphenyl)-4-n-dodecylmercaptobutane, 1,1,5,5-tetra-(5-tert-butyl-4-hydroxy-2-methylphenyl)pentane.

1.6. O—N— and S-benzyl compounds, for example 3,5,3',5'-tetra-tert-butyl-4,4'-dihydroxydibenzyl ether, octadecyl 4-hydroxy-3,5-dimethylbenzylmercaptoacetate, tris(3,5-di-tert-butyl-4-hydroxybenzyl)amine, bis(4-tert-butyl-3-hydroxy-2,6-dimethylbenzyl) dithioterephthalate, bis(3,5-di-tert-butyl-4-hydroxybenzyl)sulfide, isooctyl 3,5-di-tert-butyl-4-hydroxybenzylmercaptoacetate.

1.7. Hydroxybenzylated malonates, for example dioctadecyl 2,2-bis(3,5-di-tert-butyl-2-hydroxybenzyl)malonate, dioctadecyl 2-(3-tert-butyl-4-hydroxy-5-methylbenzyl)malonate, di-dodecyl mercaptoethyl-2,2-bis(3,5-di-tert-butyl-4-hydroxybenzyl)malonate, di-[4-(1,1,3,3-tetramethylbutyl)phenyl]2,2-bis(3,5-di-tert-butyl-4-hydroxybenzyl)malonate.

1.8. Aromatic hydroxybenzyl compounds, for example 1,3,5-tris(3,5-di-tert-butyl-4-hydroxybenzyl)-2,4,6-trimethylbenzene, 1,4-bis(3,5-di-tert-butyl-4-hydroxybenzyl)-2,3,5,6-tetramethylbenzene, 2,4,6-tris(3,5-di-tert-butyl-4-hydroxybenzyl)phenol.

1.9. Triazine compounds, for example 2,4-bisoctylmercapto-6-(3,5-di-tert-butyl-4-hydroxyanilino)-1,3,5-triazine, 2-octylmercapto-4,6-bis(3,5-di-tert-butyl-4-hydroxyanilino)-1,3,5-triazine, 2-octylmercapto-4,6-bis(3,5-di-tert-butyl-4-hydroxyphenoxy)-1,3,5-triazine, 2,4,6-tris(3,5-di-tert-butyl-4-hydroxyphenoxy)-1,2,3-triazine, 1,3,5-tris(3,5-di-tert-butyl-4hydroxybenzyl)isocyanurate, 1,3,5-tris(4-tert-butyl-3-hydroxy-2,6-dimethylbenzyl)isocyanurat, 2,4,6-tris(3,5-di-tert-butyl-4-hydroxyphenylethyl)-1,3,5-triazine, 1,3,5-tris(3,5-di-tert-butyl-4-hydroxyphenylpropionyl)hexahydro-1,3,5-triazine, 1,3,5-tris(3,5-dicyclohexyl-4-hydroxybenzyl)isocyanurate.

1.10. Benzylphosphonates, for example dimethyl 2,5-di-tert-butyl-4-hydroxybenzylphosphonate, diethyl 3,5-di-tert-butyl-4-hydroxybenzylphosphonate, dioctadecyl 3,5-di-tert-butyl-4-hydroxybenzylphosphonate, dioctadecyl 5-tert-butyl-4-hydroxy-3-methylbenzylphosphonate, the calcium salt of the monoethyl ester of 3,5-di-tert-butyl-4-hydroxybenzylphosphonic acid.

1.11. Acylaminophenols, for example 4-hydroxylauranilide, 4-hydroxystearanilide, octyl N-(3,5-di-tert-butyl-4-hydroxyphenyl)carbamate.

1.12. Esters β(3,5-di-tert-butyl-4-hydroxyphenyl) propionic acid with mono- or polyhydric alcohols, e,g, with methanol, ethanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxalamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.13. Esters of β-(5-tert-butyl-4-hydroxy-3-methylphenyl)propionic acid with mono- or polyhydric alcohols, e.g. with methanol, ethanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl) oxalamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.14. Esters of β-(3,5dicyclohexyl-4-hydroxyphenyl) propionic acid with mono- or polyhydric alcohols, e.g. with methanol, ethanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)-oxalamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.15 Esters of 3,5-di-tert-butyl-4-hydroxyphenyl acetic acid with mono- or polyhydric alcohols, e.g. with methanol, ethanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxalamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.16. Amides of β-(3,5-di-ter-butyl-4-hydroxyphenyl) propionic acid e.g. N,N'-bis(3,5-di-tert-butyl-4-hydroxyphenyipropionyl)hexamethylenediamine, N,N'-bis(3,5-di-tert-butyl-4-hydroxyphenylpropionyl) trimethylenediamine, N,N'-bis(3,5-di-tert-butyl-4-hydroxyphenylpropionyl)hydrazine.

2. UV-absorbers and light stabilizers 2.1. 2-(2'-Hydroxyphenyl)benzotriazoles, for example 2-(2'-hydroxy-5'-methylphenyl)benzotriazole, 2-(3',5'-di-tert-butyl-2'-hydroxyphenyl)benzotriazole, 2-(5'-tert-butyl-2'hydroxyphenyl)benzotriazole, 2-(2'-hydroxy-5'-(1,1,3,3-tetramethylbutyl)phenyl)benzotriazole, 2-(3',5'-di-tert-butyl-2'-hydroxyphenyl)-5-chlorobenzotriazole, 2-(3'-tert-butyl 2'-hydroxy-5'-methylphenyl)-5-chlorobenzotriazole, 2-(3'-sec-butyl-5'-tert-butyl-2'-hydroxyphenyl) benzotriazole, 2-(2'-hydroxy-4'-octoxyphenyl) benzotriazole, 2-(3',5'-di-tert-amyl-2'-hydroxyphenyl) benzotriazole, 2-(3',5'-bis(α,α-dimethylbenzyl)-2'-hydroxyphenyl)benzotriazole, a mixture of 2-(3'-tert-butyl-2'-hydroxy-5'-(2-octyloxycarbonylethyl)phenyl)-5chlorobenzotriazole, 2-(3'-tert-butyl-5'-[2-(2-ethylhexyloxy)carbonylethyl]-2'-hydroxyphenyl)-5-chlorobenzotriazole, 2-(3'-tert-butyl-2'-hydroxy-5'-(2-methoxycarbonylethyl)phenyl)-5-chlorobenzotriazole, 2-(3'-tert-butyl-2'-hydroxy-5'-(2-methoxycarbonylethyl) phenyl)benzotriazole, 2-(3'-tert-butyl-2'-hydroxy-5'-(2-octyloxycarbonylethyl)phenyl)benzotriazole, 2-(3'-tert-butyl-5'[2(2-ethylhexyloxy)carbonylethyl]-2'-hydroxyphenyl)benzotriazole, 2-(3'-dodecyl-2'-hydroxy-5'-methylphenyl)benzotriazole, and 2-(3'-tert-butyl-2'-hydroxy-5'-(2-isooctyloxycarbonylethyl) phenylbenzotriazole, 2,2'-methylenebis[4-(1,1,3,3-tetramethylbutyl)-6-benzotriazol-2-ylphenol]; the transesterification product of 2-[3'-tert-butyl-5'-(2-methoxycarbonylethyl)-2'-hydroxyphenyl]benzotriazole with polyethylene glycol 300; Compounds of the formula [R—CH$_2$CH$_2$—COO(CH$_2$)$_3$]$_2$ where R=3'-tert-butyl-4'-hydroxy-5'-2H-benzotriazol-2-ylphenyl.

2.2. 2-Hydroxybenzophenones, for example the 4-hydroxy, 4-methoxy, 4-octoxy, 4-decyloxy, 4-dodecyloxy, 4-benzyloxy, 4,2',4'-trihydroxy and 2'-hydroxy-4,4'-dimethoxy derivative.

2.3. Esters of substituted or unsubstituted benzoic acids, for example 4-tert-butyl-phenyl salicylate, phenyl salicylate, octylphenyl salicylate, dibenzoylresorcinol, bis(4-tert-butylbenzoyl)resorcinol, benzoylresorcinol, 2,4-di-tert-butylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, 2-methyl-4,6-di-tert-butylphenyl 3,5-di-tert-butyl-4-hydroxybenzoate.

2.4. Acrylates, for example ethyl α-cyano-β,β-diphenylacrylate or isooctyl α-cyano-β,β-diphenylacrylate, methyl α-carbomethoxycinnamate, methyl α-cyano-β-methyl-p-methoxy-cinnamate or butyl α-cyano-β-methyl-p-methoxycinnamate, methyl α-carbomethoxy-p-methoxycinnamate and N-(β-carbomethoxy-β-cyanovinyl)-2-methylindoline.

2.5. Nickel compounds, for example nickel complexes of 2,2'-thio-bis-[4-(1,1,3,3-tetramethylbutyl)phenol], such as the 1:1 or 1:2 complex, with or without additional ligands such as n-butylamine, triethanolamine or N-cyclohexyldiethanolamine, nickel dibutyldithiocarbamate, nickel salts of monoalkyl esters, such as of the methyl or ethyl ester, of 4-hydroxy-3,5-di-tert-butylbenzylphosphonic acid, nickel complexes of ketoximes, e.g. of 2-hydroxy-4-methylphenyl undecyl ketoxime, nickel complexes of 1-phenyl-4-1auroyl-5-hydroxypyrazole, with or without additional ligands.

2.6. Sterically hindered amines, for example bis(2,2,6,6-tetramethylpiperidyl)sebacate, bis(2,2,6,6-tetramethylpiperidyl)succinate, bis(1,2,2,6,6-pentamethylpiperidyl)sebacate, bis(1,2,2,6,6-pentamethylpiperidyl)n-butyl 3,5-di-tert-butyl-4-hydroxybenzylmalonate, the condensate of 1-hydroxyethyl-2,2,6,6-tetramethyl-4-hydroxypiperidine and succinic acid, the condensate of N,N'-bis(2,2,6,6-tetramethyl-4-piperidyl) hexamethylenediamine and 4-tert-octylamino-2,6-dichloro-1,3,5-s-triazine, tris(2,2,6,6-tetramethyl-4-piperidyl) nitrilotriacetate, tetrakis(2,2,6,6-tetramethyl-4-piperidyl)1,2,3,4-butanetetraoate, 1,1'-(1,2-ethanediyl)bis(3,3,5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperidyl)-2-n-butyl-2-(2-hydroxy-3,5-di-tert-butylbenzyl)malonate, 3-n-octyl-7,7,9,9-tetramethyl-1,3,8-triazaspiro[4.5]decan-2,4-dione, bis(1-octyloxy-2,2,6,6-tetramethylpiperidyl) sebacate, bis(1-octyloxy-2,2,6,6-tetramethylpiperidyl) succinate, the condensate of N,N'-bis-(2,2,6,6-tetramethyl-4-piperidyl)hexamethylenediamine and 4-morpholino-2,6-dichloro-1,3,5-triazine, the condensate of 2-chloro-4,6-di(4-n-butylamino-2,2,6,6-tetramethylpiperidyl)-1,3,5-triazine and 1,2-bis(3-aminopropylamino)ethane, the condensate of 2-chloro-4,6-di-(4-n-butylamino-1,2,2,6,6-pentamethylpiperidyl)-1,3,5-triazine and 1,2-bis-(3-aminopropylamino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl)pyrrolidin-2,5-dione.

2.7. Oxalamides, for example 4,4'-dioctyloxyoxanilide, 2,2'-diethoxyoxanilide, 2,2'-dioctyloxy-5,5'-di-tert-butoxanilide, 2,2'-didodecyloxy-5,5'-di-tert-butyloxanilide, 2-ethoxy-2'-ethyloxanilide, N,N'-bis(3-dimethylaminopropyl)oxalamide, 2-ethoxy-5-tert-butyl-2'-ethyloxanilide and its mixture with 2-ethoxy-2'-ethyl-5,4'-di-tert-butoxanilide and mixtures of o- and p-methoxy and of o- and p-ethoxy-disubstituted oxanilides.

2.8. 2-(2-Hydroxyphenyl)-1,3,5-triazines, for example 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis (2,4-dimethylphenyl)-1,3,5-triazine, 2-[2-hydroxy-4-(2-hydroxy-3-butyloxypropyloxy)phenyl]-4,6-bis(2,4-dimethylphenyl)-1,3,5-triazine, 2-[2-hydroxy-4-(2-hydroxy-3-octyloxypropyloxy)-phenyl]-4,6-bis(2,4-dimethylphenyl)-1,3,5-triazine.

3. Metal deactivators, for example, N,N'-diphenyloxalamide, N-salicylal-N'-salicyloyl hydrazine, N,N'-bis(salicyloyl)hydrazine, N,N'-bis(3,5-di-tert-butyl-4-hydroxyphenyl-propionyl)hydrazine, 3-salicyloylamino-1,2,4-triazole, bis(benzylidene)oxalyl dihydrazide, oxanilide, isophthaloyl dihydrazide, sebacoyl bisphenylhydrazide, N,N'-diacetyladipoyl dihydrazide, N,N'-bis(salicyloyl)oxalyl dihydrazide, N,N'-bis(salicyloyl)thiopropionyl dihydrazide.

4. Further phosphites and phosphonites, for example triphenyl phosphite, diphenyl alkyl phosphites, phenyl dialkyl phosphites, tris(nonylphenyl)phosphite, trilauryl phosphite, trioctadecyl phosphite, distearyl pentaerythritol diphosphite, tris(2,4-di-tert-butylphenyl)phosphite, diisodecyl pentaerythritol diphosphite, bis(2,4-di-tert-butylphenyl)pentaerythritol diphosphite, bis(2,6-di-tert-butyl-4-methylphenyl)pentaerythritol diphosphite, bisisodecyloxypentaerythritol diphosphite, bis(2,4-di-tert-butyl-6-methylphenyl)pentaerythritol diphosphite, bis-(2,4,6-tri-tert-butylphenyl)pentaerythritol diphosphite, tristearyl sorbitol triphosphite, tetrakis(2,4-di-tert-butylphenyl)4,4'-biphenylene diphosphonite, 6-isooctyloxy-2,4,8,10-tetra-tert-butyl-12H-dibenzo[d,g]-1,3,2-dioxaphosphocin, 6-fluoro-2,4,8,10-tetra-tert-butyl-12-methyl-dibenzo[d,g]-1,3,2-dioxaphosphocin, bis(2,4-di-tert-butyl-6-methylphenyl)methyl phosphite, bis(2,4-di-tert-butyl-6-methylphenyl)ethyl phosphite.

5. Peroxide scavengers, for example esters of β-thiodipropionic acid, for example the lauryl, stearyl, myristyl or tridecyl esters, mercaptobenzimidazole, the zinc salt of 2-mercaptobenzimidazole, zinc dibutyldithiocarbamate, dioctadecyl disulfide, pentaerythritol tetrakis(β-dodecylmercapto)propionate.

6. Polyamide stabilizers, for example copper salts in combination with iodides and/or phosphorus compounds and salts of divalent manganese.

7. Basic co-stabilizers, for example melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids, for example calcium stearate, zinc stearate, magnesium behenate, magnesium stearate, sodium ricinoleate, potassium palmitate, antimony pyrocatecholate or tin pyrocatecholate.

8. Nucleating agents, for example 4-tert-butylbenzoic acid, adipic acid, diphenylacetic acid.

9. Fillers and reinforcing agents, for example calcium carbonate, silicates, glass fibres, asbestos, talc, kaolin, mica, barium sulfate, metal oxides and hydroxides, carbon black, graphite.

10. Other additives, for example plasticizers, lubricants, emulsifiers, pigments, optical brighteners, flameproofing agents, antistatic agents, blowing agents.

11. Benzofuranones and indolinones, for example those disclosed in U.S. Pat. No. 4,325,863 or U.S. Pat. No. 4,338,244.

Of particular importance are stabilized polymers which contain an additional quantity of a light stabilizer from the class of the sterically hindered amines and/or from the class of the 2-(2'-hydroxyphenyl)benzotriazoles. Sterically hindered amines are understood as meaning in particular those compounds containing one or more groups of the formula

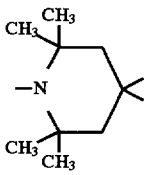

in the molecule, it being possible for these compounds to be monomeric, oligomeric or polymeric. Examples of such compounds can be found in Section 2.6 above of the list of possible additional stabilizers.

The addition of the compounds of formula (1) and, if desired, of further additives to the polymers can take place before or during shaping of the polymers, for example by mixing in powder form or by addition to the melt or solution of the polymer or to a suitable coating formulation containing a polymeric binder.

Accordingly the invention also provides the polymers stabilized by the addition of at least one compound of the formula (1), which polymers can, if desired, also contain other additives. The polymers thus stabilized can be used in various forms, for example as fibres, films, fibrous tapes, profiles, hollow articles, sheets, double-walled sheets or as binders for coatings, paints, adhesives and cements. Their use in coatings is of particular interest.

The novel UV absorbers are additionally suitable as light stabilizers in cosmetic preparations, for example for hair- or skin-dressing.

The invention, consequently, additionally provides a cosmetic preparation comprising at least one compound of the general formula (1) and cosmetically acceptable excipients or auxiliaries.

For cosmetic use the light stabilizers according to the invention usually have a mean particle size in the range from 0.02 to 2μ, preferably from 0.05 to 1.5μ and very particularly from 0.1 to 1.0μ. The insoluble UV absorbers according to the invention can be brought to the desired particle size by customary methods, for example milling using a jet, ball, vibration or hammer mill, for example. Milling is preferably carried out in the presence of from 0.1 to 30% by weight, preferably from 0.5 to 15% by weight, based on the UV absorber, of a milling aid such as, for example, an alkylated vinylpyrrolidone polymer, a vinylpyrrolidone-vinyl acetate copolymer, an acyl glutamate or, in particular, a phospholipid.

In addition to the UV absorbers according to the invention, the cosmetic preparations may also contain one or more further UV absorbers, examples being oxanilides, triazoles, vinyl-containing amides or cinnamides.

Examples of suitable oxanilides are compounds of the formula

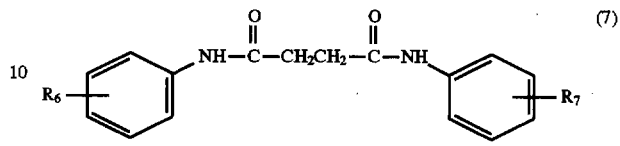

in which $R_6$ and $R_7$ independently of one another are $C_1$–$C_{18}$alkyl or $C_1$–$C_{18}$alkoxy.

Preferred triazole compounds are of the formula

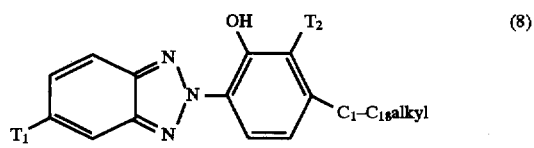

in which $T_1$ is $C_1$–$C_{18}$alkyl or, preferably, hydrogen; and $T_2$ is unsubstituted or phenyl-substituted $C_1$–$C_{18}$alkyl.

A further class of triazole compounds is of the formula

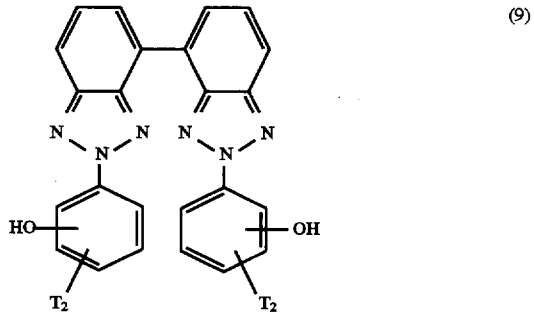

in which $T_2$ is as defined for formula (8).

Preferred vinyl-containing amides are of the formula

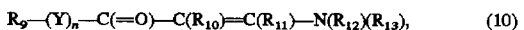

in which $R_9$ is $C_1$–$C_{18}$alkyl, preferably $C_1$–$C_5$alkyl or phenyl, phenyl being substituted by two or three substituents selected from hydroxyl, $C_1$–$C_{18}$alkyl or $C_1$–$C_{18}$alkoxy or a —C(=O) in which $R_8$ is $C_1$–$C_{18}$alkyl;

$R_{10}$, $R_{11}$, $R_{12}$ and $R_{13}$ independently of one another are hydrogen or $C_1$–$C_{18}$alkyl;

Y is N or O; and n is 0 or 1.

Preferred cinnamic acid derivatives are of the formula

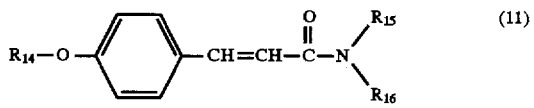

in which $R_{14}$ is hydroxyl or $C_1$–$C_4$alkoxy, preferably methoxy or ethoxy;

$R_{15}$ is hydrogen or $C_1$–$C_4$alkyl, preferably methyl or ethyl;

$R_{16}$ is —(CONH)$_n$-phenyl, n is 0 or 1 and the phenyl ring can be unsubstituted or substituted by one, two or three substituents selected from OH, $C_1$–$C_{18}$alkyl or $C_1$–$C_{18}$alkoxy or a —C(=O)—OR$_8$ group in which $R_8$ is as defined above.

The additional UV absorbers employed in addition to the UV absorbers according to the invention are known for example from Cosmetics & Toiletries (107), p. 50 ff (1992).

The cosmetic composition according to the invention contains from 0.1 to 15% by weight, preferably from 0.5 to 10% by weight, based on the overall weight of the composition, of a UV absorber or of a mixture of UV absorbers and a cosmetically acceptable auxiliary.

The cosmetic composition can be prepared by physical mixing of the UV absorber(s) with the auxiliary by customary methods, for example by simple stirring together of the two materials.

The cosmetic preparation according to the invention can be formulated as a water-in-oil or oil-in-water emulsion, as an oil-in-oil alcohol lotion, as a vesicular dispersion of an ionic or nonionic amphiphilic lipid, as a gel, as a solid stick or as an aerosol formulation.

As a water-in-oil or oil-in-water emulsion the cosmetically acceptable auxiliary preferably contains from 5 to 50% of an oil phase, from 5 to 20% of an emulsifier and from 30 to 90% of water. Said oil phase can contain any oil suitable for cosmetic formulations, for example one or more hydrocarbon oils, a wax, a natural oil, a silicone oil, a fatty acid ester or a fatty alcohol. Preferred mono- or polyols are ethanol, isopropanol, propylene glycol, hexylene glycol, glycerol and sorbitol.

For the cosmetic formulations according to the invention it is possible to use any conventionally employable emulsifier, for example one or more ethoxylated esters of natural derivatives, for example polyethoxylated esters of hydrogenated castor oil, or a silicon oil emulsifier such as silicone polyol, for example; an unmodified or ethoxylated fatty acid soap; an ethoxylated fatty alcohol; an unmodified or ethoxylated sorbitan ester; an ethoxylated fatty acid; or an ethoxylated glyceride.

The cosmetic formulation can also contain other components, examples being emollients, emulsion stabilizers, dermal moisturizers, tanning accelerators, thickeners, for example xanthan, moisture retainers, for example glycerol, preservatives, fragrances and colourants.

The cosmetic formulations according to the invention are notable for excellent protection of the human skin against the damaging effect of sunlight while providing at the same time for safe tanning of the skin. Furthermore, the cosmetic preparations according to the invention are water-resistant when applied to the skin.

In the examples below the percentages are by weight. The quantities of the colourants and triazine compounds are based on the pure substance.

EXAMPLE 1

2-(2-Hydroxyphenyl)-4,6-bis(4-methoxyphenyl)-1,3,5-triazine 42 g of 4-methoxybenzamidine hydrochloride are first introduced into 100 ml of dimethylacetamide. 41.2 ml of a 30% sodium methylate solution are added with stirring. After further addition of 33 g of methyl salicylate the mixture is heated to 90 to 95 C. and is stirred at this temperature for 20 hours. During the first three hours, about 62 ml of a mixture of methanol, dimethylacetamide and water distil off. 150 ml of methanol are added, the reaction mixture is cooled to 5 C. and the product is filtered off. Drying at 110 C. gives 30.6 g of a pale yellow product of the formula

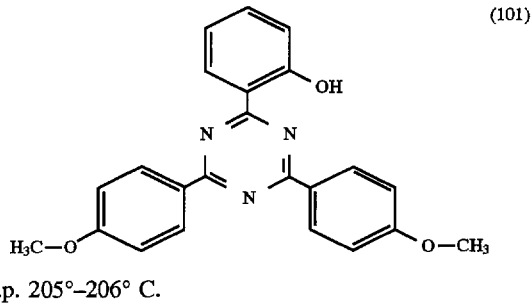

m.p. 205°–206° C.

EXAMPLES 2 to 5

The compounds of the formulae (102)–(105) in Table 1 are prepared by the same method.

TABLE 1

| Example | Compound | $R_1$ | $R_2$ | $R_3$ | m.p. [C.] |
|---|---|---|---|---|---|
| 2 | (102) | H | OH | H | 251–252 |
| 3 | (103) | CH$_3$ | H | H | 192–194 |
| 4 | (104) | H | CH$_3$ | H | 211–212 |
| 5 | (105) | H | H | Cl | 242–243 |

EXAMPLE 6a 37.2 g of 4-methoxybenzamidine hydrochloride are first introduced together with 100 ml of methanol. 36 g of a 30% sodium methylate solution in methanol and 15.2 g of o-vanillin are then added. The mixture is stirred at 50 C. for 20 hours, then cooled, and 100 ml of water are added. After washing with a 1:1 mixture of methanol/water and drying at 100 C., 34 g of a pale beige product of the formula

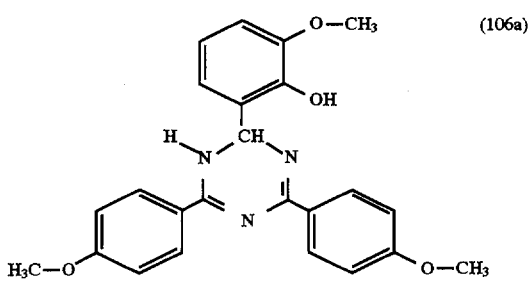

are obtained.

EXAMPLE 6b 32 g of the dihydro product (106a) in 600 ml of acetone are first introduced together with 18.9 g of chloranil and the resulting mixture is stirred at room temperature for 20 hours. Isolation of the product by filtration and drying give 27.5 g of a light-coloured product of the formula

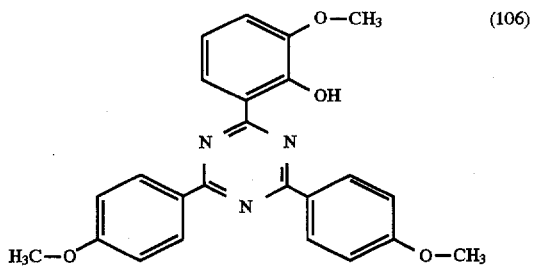
(106)

Yield: 86.4% of theory
m.p.: 197°–198° C.

EXAMPLE 7

2-(2-Hydroxy-4-methoxyphenyl)-4,6-bis(4-methoxyphenyl)-1,3,5-triazine

The procedure of Example 6 is repeated except that 2-hydroxy-4-methoxybenzaldehyde is used instead of o-vanillin. This produces the corresponding dihydro product of the formula

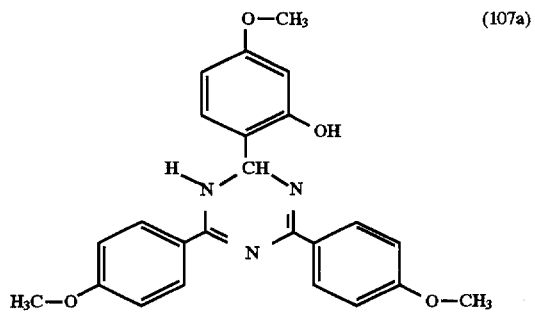
(107a)

in a yield of 41% of theory. Oxidation with chloranil gives the compound of the formula

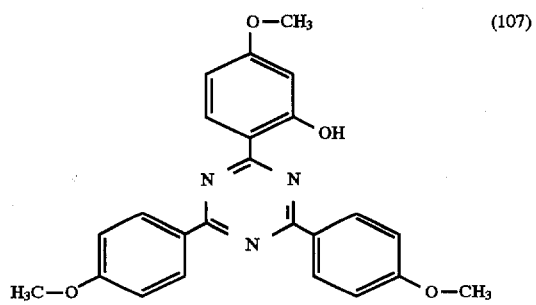
(107)

Yield: 77% of theory.
m.p.: 213–214 C.

EXAMPLE 8a

2-Chloro-4,6-bis(4-methoxyphenyl)-1,3,5-triazine

A Grignard solution of p-methoxyphenylmagnesium bromide (prepared from 12.2 g (0.05 mol) of magnesium and 93.5 g (0.5 mol) of p-bromoanisole in 130 ml of anhydrous THF) is added to a solution of 31.3 g (0.17 mol) of cyanuric chloride in 100 ml of THF over the course of 1.5 hours, while maintaining the temperature in the range from 0 to 20 C. After addition is complete, the mixture is stirred at room temperature for 1.5 hours and then poured into 150 ml of 12% hydrogen chloride solution in an icebath. The beige suspension is filtered off, washed neutral with water and then washed with methanol. The crude product is recrystallized from 350 ml of toluene to give the compound of the formula

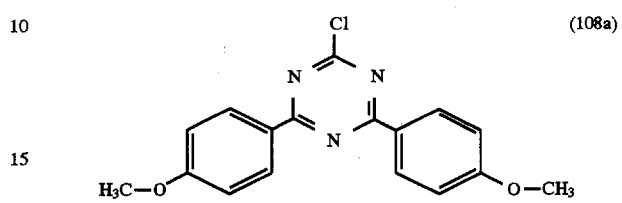
(108a)

Yield: 40 g (72% of theory)
m.p.: 193–195 C.

EXAMPLE 8b 2-(2,4-Dihydroxyphenyl)-4,6-bis(4-methoxyphenyl)-1,3,5-triazine 10.3 g (0.077 mol) of aluminium chloride are added at 5 C. to a mixture of 23.0 g (0.07 mol) of 2-chloro-4,6-bis(4-methoxyphenyl)-1,3,5-triazine of the formula (108a) and 8.5 g (0.077 mol) of resorcinol in 150 ml of toluene. The temperature is allowed to rise to 20 C., and the mixture is then heated at 50 C. for 6 hours and at reflux for 24 hours. The cooled mixture is poured into 150 ml of 12% hydrogen chloride solution, and the crude product is filtered, washed neutral with water and then washed with methanol and dried to give a dark yellow product of the formula

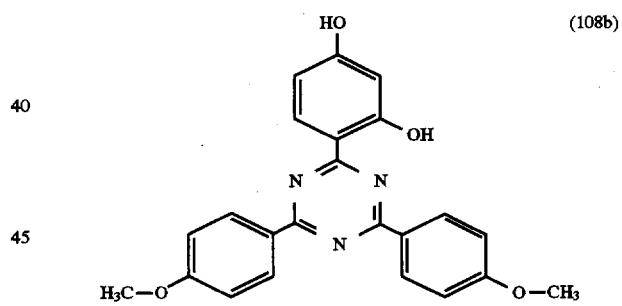
(108b)

Yield: 18.8 g (67% of theory)
m.p.: 195–198 C.

EXAMPLE 9

2-(2-Hydroxy-4-hexyloxyphenyl)-4,6-bis(4-methoxyphenyl)-1,3,5-triazine 15.2 g (0.038 mol) of 2-(2,4-dihydroxyphenyl)-4,6-bis(4-methoxyphenyl)-1,3,5-triazine of the formula (108b), 5.2 g of potassium carbonate and 50 mg of potassium iodide are heated at 110 C. in 100 ml of 2-ethoxyethanol for 45 minutes, and then 6.9 g (0.042 mol) of 1-bromohexane are added dropwise over the course of 15 minutes. The mixture is stirred at 110 C. for 12 hours, cooled to 0 C. and filtered. The solid material is washed neutral with water, then washed with methanol and dried. Recrystallization from 2-ethoxyethanol gives the pure, light-yellow product of the formula

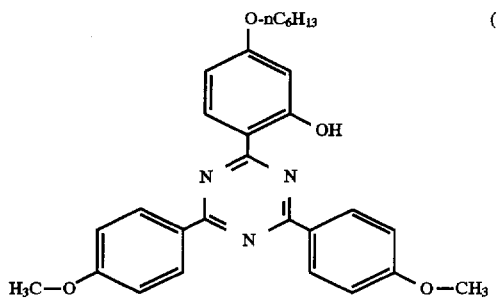

(109)

Yield: 4.8 g (26% of theory)

m.p.: 123–125 C.

EXAMPLE 10

2-(2-Hydroxy-4-hexyloxyphenyl)-4,6-bis(3-methoxyphenyl)-1,3,5-triazine 10 g (0.025 mol) of 2-(2,4-dihydroxyphenyl)-4,6-bis(3-methoxyphenyl)-1,3,5-triazine (prepared by the method of Example 8 starting from 3-bromoanisole), 3.8 g of potassium carbonate and 30 mg of potassium iodide are heated in 25 ml of 2-ethoxyethanol at 110 C. for one hour, followed by dropwise addition of 6.7 g (0.041 mol) of 1-bromohexane and stirring at 110 C. for a further 32 hours. After cooling, the mixture is filtered, the solid material is washed neutral with water and then washed with methanol and dried. The crude product is purified by column chromatography (250 g SiO₂ 35–70 μm; eluent toluene/petroleum ether 1:1). This gives the compound of formula

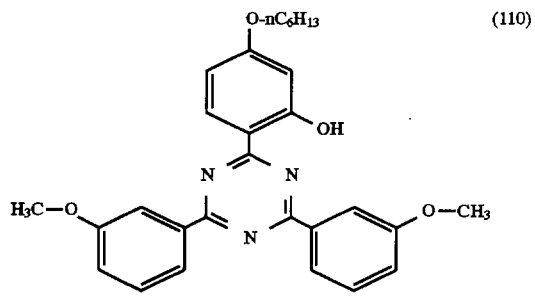

(110)

Yield: 3.4 g (28% of theory)

m.p.: 127–128 C.

EXAMPLE 11

4.9 g (10.86 mmol) of benzamidine hydrochloride (38% in methanol) and then a solution of 1.95 g (10.86 mmol) of sodium methylate (30% in methanol) are added to a suspension of 2.83 g (10 mmol) of 7-methoxy-2-(4-methoxyphenyl)-4H-1,3-benzoxazin-4-one in 48 ml of methanol. The mixture is heated to boiling and diluted with 38 ml of methanol. After boiling under reflux (30 minutes) the precipitate is filtered off with suction while hot and washed twice with 10 ml of methanol each time. Recrystallization from chloroform/petroleum ether gives 3.74 g (97% of theory) of the product of the formula

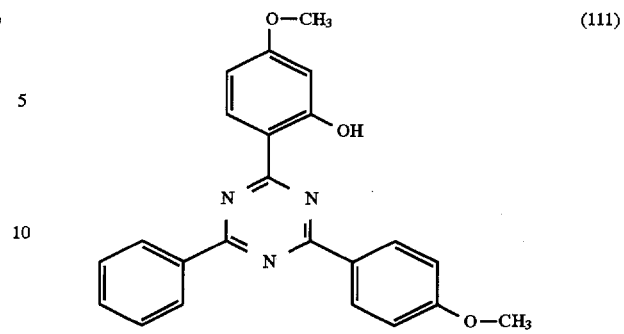

(111)

m.p.: 171–172 C.

UV spectrum (2.25×10⁻⁵ mol in chloroform)
$\lambda_{max}/\epsilon_{max}$=297/34920 325/shoulder

EXAMPLE 12

2-{4,6-bis-[4-(2-Ethylhexyloxy)phenyl]-s-triazin-2-yl}-5-(2-ethylhexyloxy)phenol a) 61.4 g (0.5 mol) of 4-hydroxybenzonitrile in 500 ml of methylcellosolve are placed in a 1 l sulfonating flask fitted with stirrer, condenser, dropping funnel and internal thermometer. The batch is heated to 80 C., and then 73.3 g of 30% NaOH (0.55 mol) are run in slowly with vigorous stirring. The mixture is stirred for 15 minutes before commencing the dropwise addition, over 30 minutes, of 116.8 g (0.575 mol) of 3-bromomethylheptane. The reaction is continued at 100 C. for about 12 hours. The thin-layer chromatogram indicates virtually quantitative conversion. Solvent and excess bromide are removed in vacuo and the residue (an oil) is taken up in 500 ml of toluene. The mixture is subjected three times to extraction by shaking with water and the extracts are dried over sodium sulfate and concentrated to dryness. High-vacuum distillation via a 10 cm Vigreux column (127–132 C., 0.15 mm) gives 97.5 g (84% of theory) of 4-(2-ethylhexyloxy)benzonitrile as a coloured oil.

b) 208.7 g (0.9 mol) of 4-(2-ethylhexyloxy)benzonitrile and 39.8 g (1.22 mol) of methanol in 400 ml of dichloroethane are placed in a 1.5 l reactor which has ground glass joints and is fitted with stirrer, condenser, internal thermometer and gas inlet tube. 85.4 g (2.37 mol) of hydrogen chloride gas are passed in over the course of 5 hours with vigorous stirring and ice-cooling (0–1 C.). After the mixture has been stirred at room temperature for 24 hours the thin-layer chromatogram indicates quantitative conversion to the imido ester. The solvent is stripped off in vacuo and the viscous yellow residue is run over the course of 30 minutes into a thoroughly stirred solution of 34 g (2.0 mol) of ammonia in 800 ml of methanol, with ice-cooling (0–10 C.). The mixture is stirred at room temperature for 1 hour and then at 50–60 C. for 90 minutes more. The mixture is concentrated to dryness in vacuo, and the oily residue is then stirred into 800 ml of hot toluene/ethanol (8:2) and filtered over silica gel. This removes a majority of the ammonium chloride produced. The filtrate is concentrated and then subjected to this purification procedure a further two times, to give 205 g (80% of theory) of amidinium salt (m.p. 172–173 C.) which still contains small quantities of ammonium chloride.

c) 113.9 g (0.4 mol) of the amidinium salt obtained in b) are suspended in a mixture of 1000 ml of distilled water and 100 ml of acetone in a 2.5 l sulfonating flask fitted with stirrer, condenser, internal thermometer, dropping funnel and pH electrode. 106.7 g of 30% sodium hydroxide solution (0.8 mol) are added slowly at 15–20 C. over the course of 30 minutes. 45.6 g (0.42 mol) of ethyl chloroformate are then added dropwise over the course of one hour (internal temperature 15–20 C.). In the course of the reaction the pH falls from 13 (initial value) to 7.0–7.5, and a particulate suspension is obtained. 500 ml of 1,2-dichlorobenzene are added and the mixture is heated to 80 C. with stirring. The organic phase is separated off in the separating funnel, transferred to a 1.5 l sulfonating flask (fitted with a Liebig condenser) and heated under a slight vacuum (about 800 mbar) to 145–175 C. (internal temperature). The urethane formed in the ring-closing condensation is distilled off (duration about 90 minutes). The brown reaction mass is run at 60 C. into 600 ml of isopropanol, and the precipitate is filtered off with suction under cold conditions (5 C.) and washed with isopropanol, water and methanol. It is subsequently dried in vacuo (100 C.). The product, 4,6-bis[4-(2-ethylhexyloxy)phenyl]-s-triazin-2-ol, shows a blue fluorescence and is uniform according to thin-layer chromatography. The yield is 57 g (56% of theory; m.p. 168–170 C.).

d) 55.6 g (0.11 mol) of 4,6-bis[4-(2-ethylhexyloxy)phenyl]-s-triazin-2-ol in 300 ml of xylene, to which 1 ml of dimethylformamide has been added, are placed in a 1.5 l sulfonating flask fitted with stirrer, cooler, internal thermometer, dropping funnel and gas outlet. 17.0 g (0.14 mol) of thionyl chloride are added dropwise at an internal temperature of 75–80 C. with vigorous stirring over the course of 15 minutes. After the evolution of gas has subsided, the temperature is raised to 100 C. The reaction is complete after 2 hours (checking by thin-layer chromatography). Excess thionyl chloride is distilled off from the reaction vessel under a slight vacuum, and the intermediate 2-chloro-4,6-bis[4-(2-ethylhexyloxy)phenyl]-s-triazine is reacted further directly. 16.2 g (0.12 mol) of dry, sublimed aluminium chloride are introduced at 50 C. (about 1 minute), whereby the temperature rises to 65 C. The initially clear, yellow solution becomes a red, then olive suspension. 13.3 g (0.12 mol) of resorcinol are added in portions at 50–55 C. (about 10 minutes) and the mixture is then heated to 85 C. After 3 hours the thin-layer chromatogram shows no further starting material. The mixture is cooled to 70 C. and the aluminium complex is hydrolysed by slow dropwise addition of 300 ml of 5% hydrochloric acid, during which the temperature should not exceed 80 C. The solvent (xylene) is removed by steam distillation, and the oily residue is stirred with 500 ml of hot toluene and filtered over silica gel. The filtrate is digested with active charcoal and filtered again. The filtrate is dried over sodium sulfate and the solvent is distilled off. For further purification, the viscous brown residue (69 g) is dissolved in 150 ml of toluene/ethyl acetate (95/5) and subjected to column chromatography (6 cm×60 cm silica gel 60), to give 33.6 g (51% of theory) of 4-{4,6-bis[4-(2-ethylhexyloxy)phenyl]-s-triazin-2-yl}-1,3-dihydroxybenzene as a viscous yellow oil.

e) 83.7 g (0.14 mol) of 4-{4,6-bis[4-(2-ethylhexyloxy)phenyl]-s-triazin-2-yl}-1,3-dihydroxy-benzene together with 500 ml of Methylcellosolve are placed at 80 C. in a 1 l sulfonating flask fitted with stirrer, condenser, internal thermometer and dropping funnel. 18.1 g of a 30% sodium hydroxide solution (0.16 mol) are added, the mixture is stirred for 15 minutes and then a solution of 31.4 g (0.16 mol) of 3-bromomethylheptane and 30 ml of Methylcellosolve are added dropwise over 30 minutes. After stirring at 110 C. for 24 hours, alkylation is complete (thin-layer chromatogram). The mixture is evaporated to dryness under vacuum, the residue is dissolved in 500 ml of toluene and filtered, and the filtrate is subjected to extraction by shaking with water. Drying of the extracts over sodium sulfate and removal of the solvent by distillation give 100.9 g of a red-brown oil. The crude product is dissolved in 200 ml of toluene/ethyl acetate (97.5/2.5) and, for purification, is chromatographed over silica gel (10 cm×40 cm), giving 79.4 g (80% of theory) of the compound of the formula

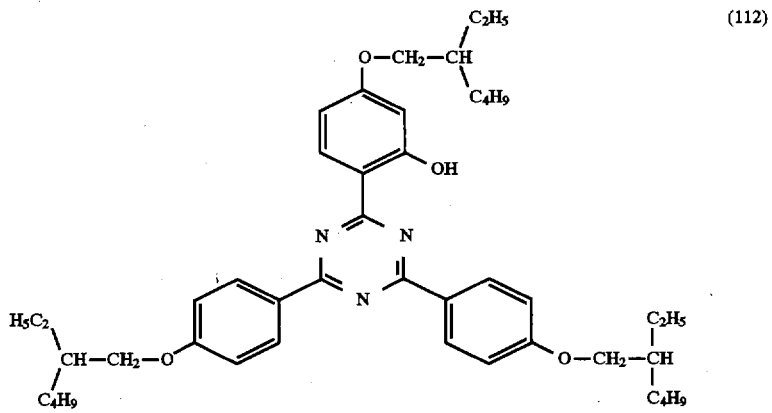

as a honeylike red-brown resin.

EXAMPLE 13

Ethyl 2-{4,6-bis[4-(2-ethylhexyloxy)phenyl]-s-triazin-2-yl}-(3-hydroxyphenoxy)acetate a) 154.1 g (1.0 mol) of 2,4-dihydroxybenzoic acid, 141.2 g (1.5 mol) of phenol, 500 ml of toluene and 1 ml of dimethylformamide are placed in a 1.5 l sulfonating flask fitted with stirrer, condenser, dropping funnel and gas outlet. 178.5 g (1.5 mol) of thionyl chloride are added dropwise over the course of 2.5 hours at an internal temperature of 100–105 C. The reddish, clear solution is then refluxed overnight (110–115 C.). Toluene and phenol are distilled off in vacuo, the highly viscous residue (271.5 g) is stirred in 300 ml of toluene/cyclohexane (7/3) and the mixture is left overnight to crystallize. The precipitate is filtered off with suction under cold conditions (10 C.) and the solid product is washed with 3×50 ml of toluene/cyclohexane (7/3) and then dried at 80 C. in vacuo, to give 125.5 g (54.4% of theory) of phenyl 2,4-dihydroxybenzoate (m.p. 135–137 C.).

b) 200 ml of absolute ethanol and 12.1 g (0.22 mol) of sodium ethanolate are introduced at room temperature into a 750 ml sulfonating flask fitted with stirrer, condenser, internal thermometer and dropping funnel. 59.9 g (0.21 mol) of amidinium hydrochloride (preparation cf. Example 12b)) are introduced and the mixture is stirred for 30 minutes. The precipitated sodium chloride is then filtered off (silica gel). A solution of 23.0 g (0.1 mol) of phenyl 2,4-dihydroxybenzoate (prepared in Example 13a)) in 100 ml of absolute ethanol is added at room temperature, and the clear red-yellow solution is stirred under reflux for 3 hours (78 C.). About 150 ml of ethanol are distilled off and the same volume of Ethylcellosolve is added. The mixture is refluxed overnight (90 C.) and concentrated to dryness in vacuo, and the residue is stirred twice with hot water and dissolved in 500 ml of toluene. After filtering the cloudy solution over silica gel, the filtrate is dried over sodium sulfate, and the solvent is stripped off in vacuo. The crude product (68.2 g) is dissolved in 120 ml of toluene and the solution is chromatographed over silica gel 60 (6 cm×60 cm) (eluent toluene/ethyl acetate 95/5). 28.5 g (48% of theory) of 4-{4,6-bis[4-(2-ethylhexyloxy)phenyl]-s-triazin-2-yl}-1,3-dihydroxybenzene are isolated as a viscous yellow oil.

c) 14.4 g (0.024 mol) of the compound prepared in b) together with 150 ml of absolute ethanol are placed in a 250 ml sulfonating flask fitted with stirrer, condenser, internal thermometer and dropping funnel at 60 C. 3.4 g of a 30% sodium hydroxide solution (0.025 mol) are added, stirring is continued for 15 minutes, and then 4.8 g (0.028 mol) of ethyl bromoacetate are added dropwise over the course of 10 minutes. After stirring under reflux for 24 hours, alkylation is complete (thin-layer chromatogram). The mixture is evaporated to dryness under vacuum, the residue is taken up in 250 ml of toluene and this mixture is subjected twice to extraction by shaking with water. Drying over sodium sulfate and removal of the solvent by distillation gives 17.1 g of a red-brown oil. The crude product is dissolved in 50 ml of toluene, for purification, the solution is chromatographed over silica gel, to give 9.0 g (55% of theory) of the compound of formula with stirrer, condenser, dropping funnel and internal thermometer. This mixture is heated to 60 C., and then 70.0 g of 30% NaOH (0.53 mol) are run in slowly. The mixture is stirred for 15 minutes and then 116.8 g (0.575 mol) of 3-bromomethylheptane are added dropwise over the course of 45 minutes. The reaction is continued at 100 C. overnight. The thin-layer chromatogram indicates virtually quantitative conversion. Solvent and excess bromide are removed in vacuo and the residue (an oil) is taken up in 600 ml of toluene. The mixture is subjected three times to extraction by shaking with water and the extracts are dried over sodium sulfate and evaporated to dryness, to give 119.3 g (84% of theory) of 4-(2-ethylhexyloxy)bromobenzene as a light yellow oil.

b) 3.65 g (0.15 mol) of magnesium turnings are placed in a 100 ml sulfonating flask fitted with stirrer, condenser, dry pipe, dropping funnel and internal thermometer under inert gas (dry nitrogen), and etching of the turnings is initiated with a few crystals of iodine. 150 ml of anhydrous tetrahydrofuran are added, and a solution of 42.8 g (0.15 mol) of 4-(2-ethylhexyloxy)bromobenzene in 30 ml of tetrahydrofuran is added dropwise over the course of 45 minutes (room temperature). After gentle heating on the waterbath (40 C.) the Grignard reaction starts up (clouding, exothermic). The mixture is stirred at 40 C. for one hour and then under reflux (66 C.) until virtually all of the magnesium has dissolved (about 30 minutes). After cooling to room temperature, the Grignard solution is added dropwise at 0–C. over the course of 60 minutes to a solution of 9.2 g (0.05 mol) of cyanuric chloride in 40 ml of tetrahydrofuran (350 ml sulfonating flask, stirrer, condenser, dry pipe, dropping funnel, internal thermometer, inert gas). The mixture is stirred under reflux (66 C.) overnight and then evaporated to dryness. The residue is stirred with 100 ml of ice-cold 2N hydrochloric acid and then subjected to extraction with 200 ml of toluene. The organic phase is shaken twice with 10% brine, dried over sodium sulfate and concentrated by evaporation. The crude product (40.3 g, red oil) is still heavily contaminated (thin-layer chromatogram). To purify it, it is dissolved in 80 ml of toluene/hexane (1/1) and the solution is chromato-

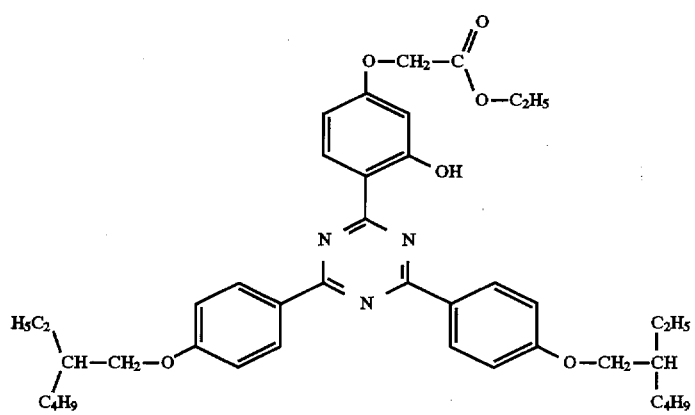

(113)

as an orange-coloured resin which crystallizes after a few days (m.p. 93–95 C.).

EXAMPLE 14

2-{4,6-bis[4-(2-ethylhexyloxy)phenyl]-s-triazin-2-yl}-5-(2-ethylhexyloxy)phenol a) 86.5 g (0.5 mol) of 4-bromophenol in 500 ml of Methylcellosolve are placed in a 1 l sulfonating flask fitted graphed over silica gel (5 cm×45 cm). 18.2 g (69.5%) of 2-chloro-4,6-bis[4-(2-ethylhexyloxy)phenyl]-s-triazine are isolated as a yellow resin.

c) The Friedel-Crafts acylation is carried out as described in Example 12d), to give 4-{4,6-bis[4-(2-ethylhexyloxy)phenyl]-s-triazin-2-yl}-1,3-dihydroxybenzene as product.

d) The alkylation is as described in Example 12e).

The end product is the compound of the formula (112).

EXAMPLES 15 TO 17

Using the methods described in Examples 12 to 14 it is also possible to obtain the following compounds (Table 2):

TABLE 2

[Structure: triazine compound with R'-substituted hydroxyphenyl group at top, and two R-O-phenyl groups at bottom]

| Example | Compound of formula | R | R' | m.p. [°C.] |
|---|---|---|---|---|
| 15 | (115) | n-dodecyl | —O—CH$_2$COC$_2$H$_5$ | yellow oil |
| 16 | (116) | n-dodecyl | n-dodecyloxy | yellow oil |
| 17 | (117) | —O—CH$_2$—CH(C$_2$H$_5$)(C$_4$H$_9$) | H | 94–95 |

EXAMPLE 18

Further Preparation Variant of the Compound of the Formula (117)

a. Preparation of 2-[4,6-bis(4-hydroxyphenyl)-s-triazin-2-yl]phenol: 9.2 g (0.4 mol) of sodium are dissolved in 200 ml of absolute ethanol in a 750 ml sulfonating flask fitted with stirrer, condenser, internal thermometer and dropping funnel, and then 72.7 g (0.4 mol; 95% pure) of 4-hydroxybenzamidinium chloride (prepared as in Example 12b)) are added at 10–15 C. The mixture is stirred at this temperature for 15 minutes (white sodium chloride suspension). Then 85.7 g (0.4 mol) of phenyl salicylate dissolved in 150 ml of absolute ethanol are slowly added. The mixture is heated to reflux temperature (78 C.), which is accompanied by the evolution of gas and leads to the formation of a yellow suspension. This suspension is refluxed overnight (18 hours) and evaporated to dryness in vacuo. The residue is stirred with 250 ml of water (alkaline suspension), rendered weakly acidic with hydrochloric acid, and again stirred with water. The semisolid mass is suspended in 50 ml of isopropanol, and the product is filtered off with suction and washed with isopropanol, before being dried in vacuo at 100 C. The crude product, which is shown by thin-layer chromatography to be still slightly contaminated, can be purified by recrystallization from dimethylformamide/water (7/3).

Yield: 40.4 g (57% of theory; colourless crystals)

The structure agrees with elemental anaysis, $^1$H-NMR and the UV spectrum.

b. Preparation of the end compound: 7.15 g (0.02 mol) of 2-[4,6-bis(4-hydroxyphenyl)-s-triazin-2-yl]phenol are placed together with 80 ml of Methylcellosolve and 3.36 g of a 50% sodium hydroxide solution (0.044 mol) in a 250 ml sulfonating flask fitted with stirrer, condenser, internal thermometer and dropping funnel. The clear yellow solution is heated to 60 C., and after stirring for 15 minutes 8.76 g (0.044 mol) of 3-(bromomethyl)heptane are added slowly (dropping funnel). After stirring at reflux for 8 hours (118 C.), alkylation is complete (thin-layer chromatogram). The mixture is evaporated to dryness in vacuo, the residue is taken up in 100 ml of toluene and the mixture is twice subjected to extraction by shaking with water. Drying over sodium sulfate and removal of the solvent by distillation give 21.0 g of a yellow paste. The crude product is dissolved in 60 ml of toluene/ethyl acetate (95:5) and, for purification, the solution is chromatographed over silica gel, to give 7.1 g (61% of theory) of product as a pale yellow resin which crystallizes after a few days (m.p. 56–57 C.; colourless crystals with a slight yellow tinge). The structure agrees with elemental analysis, $^1$H-NMR and the UV spectrum ($\lambda_{max}$= 320 nm, $\epsilon_{max}$=57,000 M$^{-1}$ cm$^{-1}$).

EXAMPLE 19

The compound of the formula (117) can also be obtained by ring closure of the corresponding 4-alkoxybenzamidine with salicylic esters in accordance with the above method.

APPLICATION EXAMPLES

EXAMPLE 20

Eight 10 g samples of a PES knitted fabric are dyed in a HT dyeing machine, for example a Labomat® from Mathis, Niederhasli, at a liquor ratio of 10:1. The liquors contain in each case 2 g/l of ammonium sulfate, 0.5 g/l of a dyeing assistant, for example ®Univadin 3-flex, and the following dyes in the quantities indicated:

0.210% of the dye (1) C.I. DISPERSE YELLOW 42
0.087% of the dye (2) C.I. DISPERSE RED 302
0.080% of the dye (3) C.I. DISPERSE VIOLET 57
0.087% of the dye (4) C.I. DISPERSE BLUE 60.

Whereas the liquor (I) does not contain any further additives (stabilizers), an additional 0.6% of the compounds listed in Table 3 by their numbers is added to the liquors (II)–(VIII).

The compounds had previously been milled to a fineness of 1–2μ with 2 parts of a nonionic dispersant in a ball mill or using a high-speed stirrer.

The pieces of knitted fabric are dyed in the dispersed liquor in pressurized autoclaves. For this purpose the dyeing liquor is entered at 50 C. and is heated after 5 minutes to 130 C. at a rate of 3 /minute. This temperature is maintained for 45 minutes. The liquor is then cooled to 50 C., and the dyed material is rinsed thoroughly with demineralized water and dried.

To determine the lightfastness, exposure is carried out in accordance with SAEJ 1885. The results are listed in Table 3.

TABLE 3

| | Liquor | Colour shift factor ΔE as determined by CieLab D 65/10 SAE J 1885 488 kJ |
|---|---|---|
| (I) | none* | 6.3 |
| (II) | 0.6% (103) | 2.8 |
| (III) | 0.6% (106) | 2.4 |
| (IV) | 0.6% (107) | 2.9 |
| (V) | 0.6% (102) | 2.5 |
| (VI) | 0.6% (104) | 2.4 |
| (VII) | 0.6% (101) | 2.0 |
| (VIII) | 0.6% (111) | 2.1 |

*mean value of 10 determinations

The results from Table 3 show that the fibre materials treated in accordance with the invention have substantially better lightfastness properties than the corresponding untreated material.

EXAMPLE 21

Application in PES Printing

In order to print a PES knitted fabric, the printing pastes listed below are prepared. The individual components making up these pastes, namely stock thickener, dye, water and the UV absorbers of the formula (101) (=paste 2) and (107) (paste 3) are mixed with one another. The compounds of the formula (101) and (107) are present as 30% formulations milled in a sand mill. Printing paste 1 contains no active substance.

Printing pastes 1,2 and 3 each contain the following individual components:
(a) 750 parts of a stock thickener consisting of
  9 parts of starch ether
  18 parts of sodium alginate
  3.75 parts of sodium dihydrogen phosphate and
  2.48 parts of sodium chlorate.
The thickener is adjusted with water to a total of 750 parts.
(b) 7.4 parts of a dye mixture consisting of
  2.4 parts of the dye C.I. Disperse Yellow 42
  2.0 parts of the dye C.I. Disperse Red 302
  2.4 parts of the dye C.I. Disperse Violet 57
  2.4 parts of the dye C.I. Disperse Blue 60
(c) UV absorber
  Paste 1: none
  Paste 2: 30 parts of the milled composition of the compound of the formula (101)
  Paste 3: 30 parts of the milled composition of the compound of the formula (107)
The 3 pastes are adjusted with water to 1000 parts in each case.

Using these printing pastes, the precleaned pieces of knitted fabric are printed on a customary commercial printing table. The samples obtained are dried at 120 C., steam-treated at 178 C. for 8 minutes, and reduction-cleaned at 70 C. for 30 minutes using 2 ml/l of NaOH (36 Be) and 3 g/l of sodium dithionite. They are then rinsed with hot and cold water, centrifuged and dried at 120 C.

The prints are tested for their lightfastness in accordance with DIN 75202 and SAE J 1885. The results obtained are as follows (Table 4):

TABLE 4

| | Lightfastness properties | |
|---|---|---|
| | 4 periods DIN 75202 | 600 kJ acc. to SAE J 1885 |
| Paste 1 | 1–2 | 1 |
| Paste 2 | 4 | 3–4 |
| Paste 3 | 3–4 | 3 |

(Rated according to grey scale 1–5):

The results from Table 4 show that the fibre materials treated in accordance with the invention (paste 2 and paste 3) have substantially better lightfastness properties than the corresponding untreated material (paste 1).

EXAMPLE 22

Application as Light Stabilizer in Cosmetics

Preparation of a O/W emulsion
Phase (A)
  3 g of the compound of the formula (112) are dissolved in
  10 g of sesame oil.
  4 g of glyceryl stearate,
  1 g of stearic acid,
  0.5 g of cetyl alcohol and
  0.2 g of Polysorbat 20 are then added and the mixture is melted.
Phase (B)
  0.005 g of propylparaben and
  0.15 g of methylparaben are dissolved in
  4 g of propylene glycol. Then
  60 ml of water are added and the mixture is heated to 70 C.
  0.1 g of Carbomer 934 is emulsified in this mixture.

Phase (A) is added slowly to phase (B) with the use of a large quantity of mechanical energy. The volume is adjusted to 100 ml by adding water.

With an addition of 3% of the UV absorber of the formula (112), the resulting emulsion has a sun protection factor (according to B. L. Diffey and J. Robson, J. Cosmet. Chem. 40, 127–133 (1989)) SPF of 17.

The sun protection factor can be altered by varying the concentration of UV absorber. Table 6 below lists light protection factors for various concentrations of the UV absorber of the formula (112):

TABLE 5

| UV absorber Compound of the formula (112) [%] | Light protection factor according to Diffey and Robson |
|---|---|
| 0.5 | 2 |
| 1 | 5 |
| 1.5 | 10 |
| 2 | 13 |
| 3 | 17 |

EXAMPLE 23

Application as a Light Stabilizer in Cosmetics 0.5 g of the UV absorber of the formula (113) and 5.5 g of the phospholipid Phospholipon 90 or Phospholipon 90H are dissolved together in 109 ml of N-methylpyrrolidone.

0.2 g of hexadecyltrimethylammonium chloride is first dissolved in 190 ml of a water/ethanol mixture (1/10) and this solution is then added to the solution of UV absorber and phospholipid. The resulting mixture is added dropwise to 2 l of aqueous 0.03% NaCl solution, to form unilamellar vesicles. The vesicle suspension is concentrated to 100 ml by diafiltration and the solvent is exchanged for aqueous 0.03% NaCl solution. Then 0.6 g of hydroxycellulose and 0.1 g of 2-bromo-2-nitropropane-1,3-thiol are added. The diameter of the vesicles is determined by photon correlation spectroscopy as being (150 50) nm. The formulation has a Diffey and Robson sun protection factor SPF of 3.

EXAMPLE 24

Application as a Light Stabilizer in Cosmetics 1.2 g of the UV absorber of the formula (117) and 6.1 g of the phospholipid Phospholipon 90 or Phospholipon 90H are dissolved together in 70 ml of N-methylpyrrolidone.

0.33 g of hexadecyltrimethylammonium chloride is first dissolved in 190 ml of a water/ethanol mixture (1/10) and this solution is then added to the solution of UV absorber and phospholipid. The resulting mixture is added dropwise to 2 l of aqueous 0.03% NaCl solution, to form unilamellar vesicles. The vesicle suspension is concentrated to 100 ml by diafiltration and the solvent is exchanged for aqueous 0.03% NaCl solution. Then 0.6 g of hydroxycellulose and 0.1 g of 2-bromo-2-nitropropane-1,3-thiol are added.

The diameter of the vesicles is determined by photon correlation spectroscopy as being (150 50) nm.

The formulation has a Diffey and Robson sun protection factor SPF of 6.

EXAMPLE 25

Use in Organic Polymers 10 g of polycarbonate powder (Lexan®115) are dissolved with stirring at room temperature in 50 g of methylene chloride, a procedure which takes several hours. To this solution is added 0.2 g of UV absorber, corresponding to a concentration of 2% of additive. These solutions are used to produce cast films with a thickness of 20 μm.

The films are exposed in an Atlas Weatherometer C165 at a black standard temperature of 63 C., a radiation energy of 0.35 W/m² at 340 nm and a relative humidity of 60%. The discoloration of the samples is measured at regular intervals by determining the yellowness index (YI, method ASTM D 1925). Table 6 indicates the exposure time which elapsed until the yellowness index was 7.

The films are then further exposed until they become brittle, which is manifested by the formation of cracks in the films. The exposure time to embrittlement is likewise listed in Table 6.

TABLE 6

| | Exposure time (h) until a yellowness index (YI) of 7 is reached and until embrittlement takes place | |
|---|---|---|
| UV absorber | Exposure time (h) | |
| of the formula | YI = 7 | To embrittlement |
| none | 590 | 1375 |
| (111) | 2100 | 5000 |
| (101) | 1480 | 4980 |
| (110) | 1850 | 4020 |

EXAMPLE 26

Use in Organic Polymers

Polycarbonate powder is mixed with 0.3% of UV absorber, and the mixture is processed at a melt temperature of 275 C. in a twin-screw extruder (25 revolutions per minute) in order to form granules.

The granules are processed in an injection moulding machine (240/300 C/75 bar) to give plates measuring 67×43×2 mm. The plates are exposed in an Atlas Weatherometer C165 as described in Example 25. Table 7 indicates the exposure time until a yellowness index (YI, measured in accordance with ASTM D-1925) of 10 and 20 is reached.

TABLE 7

| | Exposure time (h) until yellowness index (YI) of 10 and 20 is reached | | |
|---|---|---|---|
| UV absorber | | Exposure time (h) | |
| of the formula | Initial YI | to YI = 10 | to YI = 20 |
| none | 3.2 | 250 | 780 |
| 0.3% (101) | 4.4 | 950 | 2700 |

What is claimed is:

1. A hydroxyphenyl-s-triazine of the formula

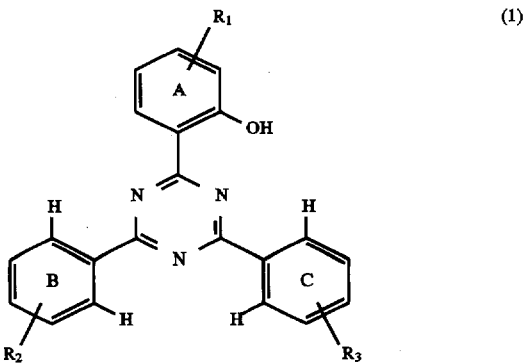

in which $R_1$ is hydrogen, hydroxyl, halogen, $C_1$-$C_{15}$alkyl, $C_1$-$C_{15}$alkoxy, a radical of the formula —O—CH$_2$—CH(—OH)—CH$_2$—O—T, in which T is $C_1$-$C_8$alkyl, or a radical of the formula

$R_2$ and $R_3$ are

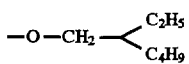

$R_4$ is $C_1$–$C_5$alkyl or $C_1$–$C_5$alkoxy-$C_1$–$C_5$alkyl, and

Q is a $C_1$–$C_4$alkylene radical, and the rings A, B and C can have further substituents.

2. A hydroxyphenyl-s-triazine according to claim 1, wherein $R_1$ is hydrogen or $C_5$–$C_{15}$alkoxy; or is a radical of the formula —O—$CH_2$—CH(—OH)—$CH_2$—O—T, in which T is $C_1$–$C_8$alkyl.

3. A hydroxyphenyl-s-triazine according to claim 1, wherein $R_1$ is hydrogen.

4. A process for preparing a hydroxyphenyl-s-triazine according to claim 1, which comprises reacting a salicylic compound of the formula

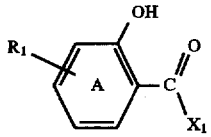 (3)

with a benzamidine compound of the formula

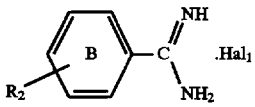 (4)

to give the triazine compound of the formula (1) where $R_1$, $R_2$, A and B are as defined for formula (1), $X_1$ is halogen or —$OR_4$, $R_4$ is $C_1$–$C_3$alkyl and $Hal_1$ is halogen.

5. A process for preparing a hydroxyphenyl-s-triazine according to claim 1, which comprises reacting a monochlorotriazine compound of the formula

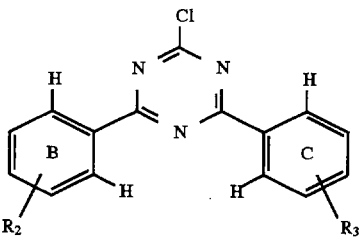 (1c)

with an α-hydroxyphenyl compound of the formula

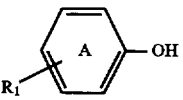 (5)

in the presence of aluminium chloride to give a triazine compound of the formula (1) in which $R_1$, $R_2$, $R_3$, $Hal_1$, A, B and C are as defined for formula (1).

6. A cosmetic preparation comprising at least one compound according to claim 1 together with cosmetically acceptable excipients or auxiliaries.

7. A preparation according to claim 6, which comprises further UV absorbers.

8. A preparation according to claim 7, which comprises additional UV abosorbers which are oxanilides, triazoles, vinyl-containing amides or cinnamamides.

* * * * *